(12) United States Patent
Kang et al.

(10) Patent No.: US 11,857,781 B2
(45) Date of Patent: *Jan. 2, 2024

(54) NEEDLE TIP FOR APPLICATION OF CURRENT, HAND PIECE, AND SKIN TREATMENT APPARATUS

(71) Applicant: JEISYS MEDICAL INC., Seoul (KR)

(72) Inventors: Dong Hwan Kang, Incheon (KR); Hye Jin Sun, Incheon (KR)

(73) Assignee: JEISYS MEDICAL INC., Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 18/185,158

(22) Filed: Mar. 16, 2023

(65) Prior Publication Data

US 2023/0218895 A1 Jul. 13, 2023

Related U.S. Application Data

(63) Continuation of application No. 17/025,618, filed on Sep. 18, 2020, now Pat. No. 11,633,592, which is a (Continued)

(30) Foreign Application Priority Data

Jul. 17, 2019 (KR) .......................... 10-2019-0086628
Jul. 17, 2020 (KR) .......................... 10-2020-0088649

(51) Int. Cl.
*A61N 1/04* (2006.01)
*A61N 1/32* (2006.01)
(Continued)

(52) U.S. Cl.
CPC ........... *A61N 1/328* (2013.01); *A61N 1/0476* (2013.01); *A61N 1/0502* (2013.01); *A61N 1/06* (2013.01)

(58) Field of Classification Search
CPC .... A61N 1/328; A61N 1/0476; A61N 1/0502; A61N 1/06
See application file for complete search history.

(56) References Cited

U.S. PATENT DOCUMENTS 11,633,592 B2 * 4/2023 Kang ...................... A61N 1/04
607/2
2007/0142885 A1 6/2007 Hantash et al.
(Continued)

FOREIGN PATENT DOCUMENTS

JP 2015-528345 A 9/2015
KR 10-2011-0118006 A 10/2011
(Continued)

OTHER PUBLICATIONS

An Office Action; "Notice of Reasons for Refusal", mailed by the Japanese Patent Office dated Jan. 18, 2022, which corresponds to Japanese Patent Application No. 2021-502779 and is related to U.S. Appl. No. 17/025,618.

*Primary Examiner* — Ankit D Tejani
*Assistant Examiner* — Joshua Brendon Solomon
(74) *Attorney, Agent, or Firm* — Studebaker & Brackett PC

(57) ABSTRACT

The inventive concept relates to a needle tip for application of current, a hand piece, and a skin treatment apparatus that are equipped with a needle in which an electromagnetically-energized active region is formed as a partial region other than a tip end of the needle is exposed in a non-insulated state.

12 Claims, 16 Drawing Sheets

Related U.S. Application Data continuation of application No. PCT/KR2020/009465, filed on Jul. 17, 2020.

(51) Int. Cl.
  *A61N 1/05* (2006.01)
  *A61N 1/06* (2006.01)

(56) References Cited

U.S. PATENT DOCUMENTS

| | | |
|---|---|---|
| 2010/0198212 A1 | 8/2010 | Sluijter et al. |
| 2012/0158100 A1 | 6/2012 | Schomacker |
| 2015/0306386 A1 | 10/2015 | Alpert et al. |
| 2017/0049513 A1 | 2/2017 | Cosman, Jr. et al. |
| 2019/0083187 A1 | 3/2019 | Danitz et al. |
| 2021/0038881 A1 | 2/2021 | Hinman et al. |

FOREIGN PATENT DOCUMENTS

| | | |
|---|---|---|
| KR | 10-2012-0126706 A | 11/2012 |
| KR | 10-2013-0045581 A | 5/2013 |
| KR | 10-1286752 B1 | 7/2013 |
| KR | 10-2019-0134222 A | 12/2019 |
| WO | 2009/059186 A1 | 5/2009 |
| WO | 2016/161201 A2 | 10/2016 |

\* cited by examiner

NEEDLE TIP FOR APPLICATION OF CURRENT, HAND PIECE, AND SKIN TREATMENT APPARATUS

CROSS-REFERENCE TO RELATED APPLICATIONS

The present application is a Continuation of U.S. patent application Ser. No. 17/025,618 filed Sep. 18, 2020, which is a Continuation of International Patent Application No. PCT/KR2020/009465, filed on Jul. 17, 2020, which is based upon and claims the benefit of priority to Korean Patent Application Nos. 10-2019-0086628 filed on Jul. 17, 2019, and 10-2020-0088649 filed on Jul. 17, 2020. The disclosures of the above-listed applications are hereby incorporated by reference herein in their entirety.

BACKGROUND

Embodiments of the inventive concept described herein relate to a needle tip for application of current, a hand piece, and a skin treatment apparatus that are equipped with a needle in which an electromagnetically-energized active region is formed as a partial region other than a tip end of the needle is exposed in a non-insulated state.

In general, the skin of a person serves as a primary barrier against environmental influences such as the sun, cold, wind, and the like. As the person grows older, due to the environmental influences, the skin loses its vital appearance and has wrinkles.

The skin is constituted by an epidermal layer having a thickness of about 100 μm, a dermal layer located under the epidermal layer and having a thickness of about 4 mm, and a subcutaneous layer located under the dermal layer.

The dermal layer is constituted by collagen, glycosaminoglycan, and proteoglycan, and the subcutaneous layer has elastic fibers connecting the collagen of the dermal layer and the top and bottom of the subcutaneous layer.

Here, the collagen and the elastic fibers may provide stiffness and elasticity to the skin, but may lose the stiffness and the elasticity depending on skin aging and exposure to sunlight. As a result, the vitality of the skin may be decreased. Accordingly, skin treatment apparatuses for revitalizing skin have been developed.

The skin treatment apparatuses are intended to treat various scars or skin diseases or treat skin for cosmetic purposes such as skin improvement or wrinkle improvement. By transferring various energy sources to the skin, the skin treatment apparatuses induce an injury to the skin and stimulate collagen of the skin to induce regeneration of the collagen.

Various types of skin treatment apparatuses, such as an HIFU type skin treatment apparatus that transfers ultrasonic waves, an RF type skin treatment apparatus that transfers electrical energy, an optical type skin treatment apparatus that transfers laser light, and the like exist.

Among the skin treatment apparatuses, the RF type skin treatment apparatus, which transfers electrical energy, applies RF current after inserting an insulated needle or a non-insulated needle into skin. As a result, electrical energy is transferred a deep skin portion through the insulated needle or the non-insulated needle.

FIGS. 1 and 2 are views illustrating needles used in an existing skin treatment apparatus.

In the related art, an insulated needle 10 of FIG. 1 and a non-insulated needle 30 of FIG. 2 are inserted into an epidermal layer 21 and a dermal layer 22 of skin 20, and electrical (RF) energy is applied to a region of the skin 20 to be treated. However, due to a characteristic that electrical energy is concentrated on a sharp end, energy tends to be concentrated on a needle end. Accordingly, electrical energy tends to be concentrated, with tip ends of the insulated needle 10 and the non-insulated needle 30 as the centers, in which the remainder of the insulated needle 10 other than a tip end 12 is coated with an insulating material 11. Therefore, laceration is excessively generated in only the region of the skin 20 where the tip ends are located.

Furthermore, the insulated needle 10 can transfer electrical energy only to the skin 20 in which the tip end 12 is located, and cannot transfer electrical energy to the skin 20 located on a side surface of the needle.

Moreover, because the entire region 31 of the non-insulated needle 30 is not coated with an insulating material, electrical energy can be transferred to a side surface of the needle. However, as the electrical energy is transferred to all surfaces making contact with the needle, the total energy is increased, and excess energy is caused. Also, the electrical energy may be concentrated on the tip end of the non-insulated needle 30 as mentioned above, which causes an unnecessary pain.

In addition, the non-insulated needle 30 cannot transfer electrical energy only to a specific depth of the skin 20 and transfers electrical energy to the entire region into which the needle is inserted. Therefore, it is difficult to treat only the skin 20 corresponding to a specific target depth.

SUMMARY

Embodiments of the inventive concept provide a needle tip for application of current that is capable of supplying electrical energy only to a specific depth of skin.

Embodiments of the inventive concept provide a needle tip for application of current that is capable of preventing excessive electrical energy concentrated on a tip end of a needle from being transferred to skin.

The problems to be solved by the inventive concept are not limited to the aforementioned problems, and any other problems not mentioned herein will be clearly understood from the following description by those skilled in the art to which the inventive concept pertains.

According to an exemplary embodiment, a needle tip for application of current includes a needle fixing part and a plurality of needles disposed on one surface of the needle fixing part. Each of the needles includes a first insulated region formed at a tip end, and at least one active region and at least one second insulated region formed in the remaining portion, and current is applied to the plurality of needles. The active region is exposed and electromagnetically energized, and the first insulated region and the second insulated region are coated with an insulating material.

Needles adjacent to each other among the plurality of needles may output different polarities or the same polarity. The at least one active region of each of the needles may be disposed at the same height, and electrical energy may be supplied to a specific depth of skin through an energy transfer region formed between the active regions of the needles.

The active regions may be formed to have the same size. The size by which the energy transfer region is formed in the skin may be adjusted by adjusting the strength of the current applied to the plurality of needles.

When the plurality of needles have a plurality of active regions spaced apart from each other, a plurality of energy transfer regions formed between the plurality of active regions may be spread by adjusting the strength of the current applied to the plurality of needles to 20 W to 50 W.

One of two needles adjacent to each other among the plurality of needles may output a positive (+) polarity, and the other may output a negative (−) polarity.

According to an exemplary embodiment, a hand piece includes the above-described needle tip for application of current mounted thereon.

According to an exemplary embodiment, a skin treatment apparatus includes a casing that suctions a target region of a surface of skin, a cartridge mounted on one side of the casing, the needle tip for application of current of claim 1 that is disposed in the cartridge, an actuator that reciprocally moves the needle tip for application of current into or out of the cartridge, an electricity supply device that applies current to a plurality of needles of the needle tip for application of current, and a controller that controls the actuator and the electricity supply device.

The cartridge may have a first space formed between a contact surface brought into close contact with the skin and a needle fixing part of the needle tip for application of current, and negative pressure may be formed in the first space before the needles are inserted into the skin.

According to an exemplary embodiment, a method for manufacturing the needle tip for application of current includes preparing a conductive material having a thickness by which an active region corresponding to a non-insulated region is to be formed, coupling a plurality of needles to a needle fixing part, inserting the plurality of needles into the conductive material up to locations of the plurality of needles where the active region is desired to be formed, and forming a first insulated region and a second insulated region by spraying an insulating material in a state in which the plurality of needles are inserted into the conductive material.

BRIEF DESCRIPTION OF THE FIGURES

The above and other objects and features will become apparent from the following description with reference to the following figures, wherein like reference numerals refer to like parts throughout the various figures unless otherwise specified, and wherein.

DETAILED DESCRIPTION

Figure 1:
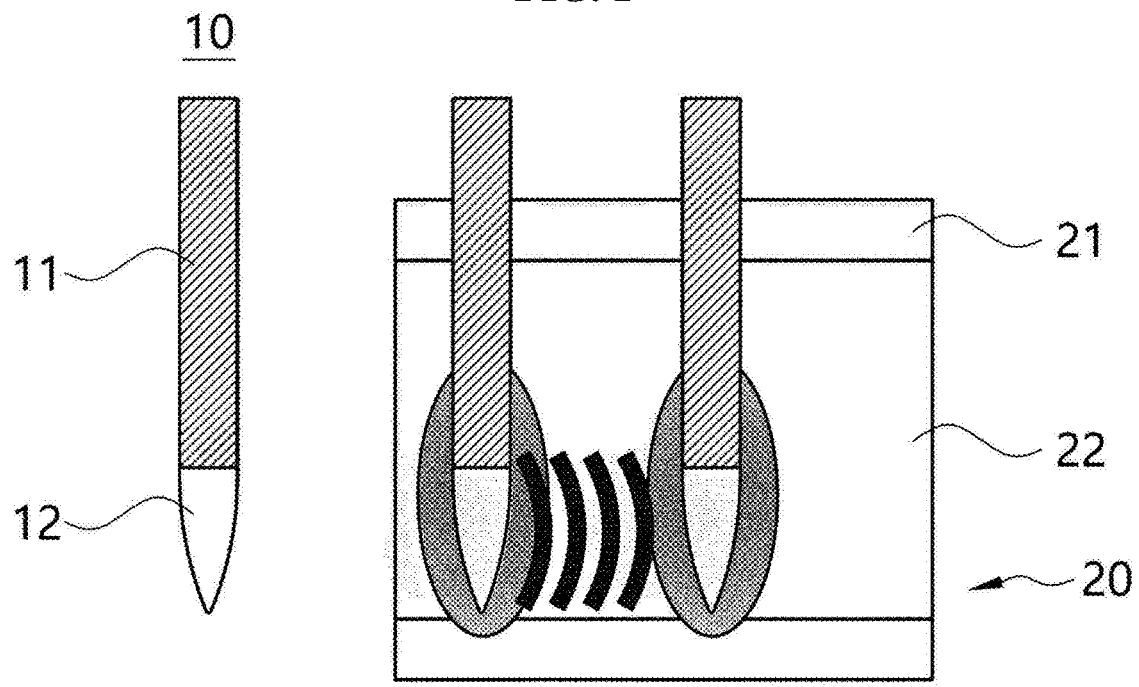
FIGS. 1 and 2 are views illustrating needles used in an existing skin treatment apparatus.
Figure 2:
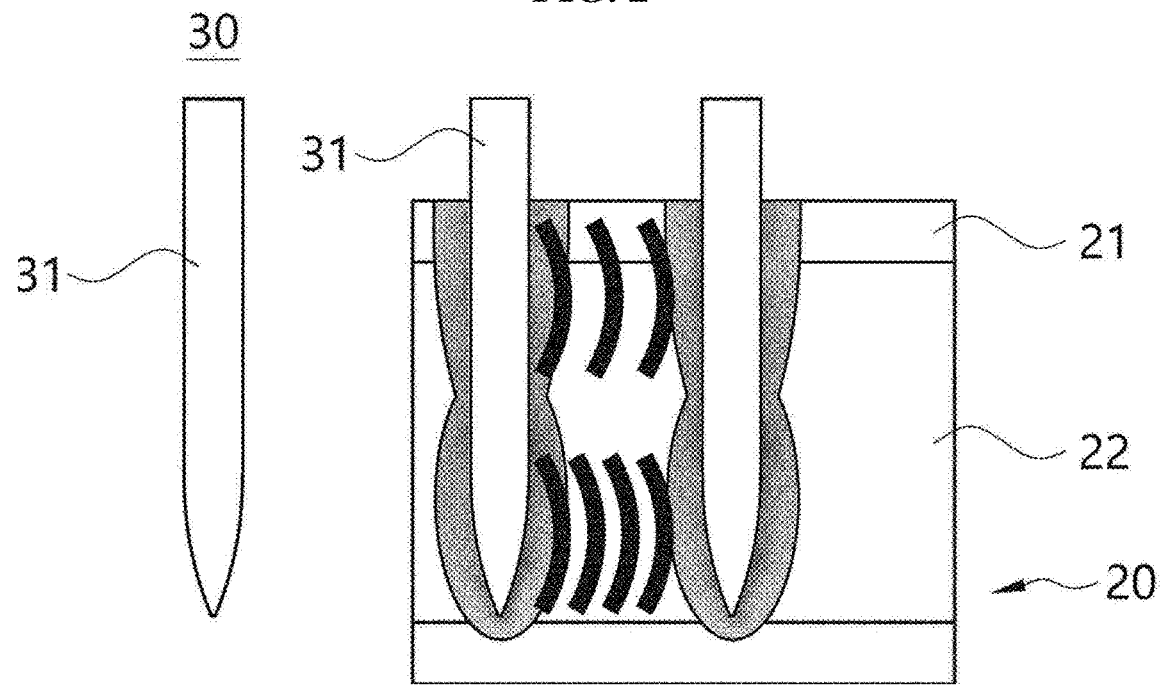

The above and other aspects, features, and advantages of the inventive concept will become apparent from the following description of embodiments given in conjunction with the accompanying drawings. However, the inventive concept is not limited to the embodiments disclosed herein and may be implemented in various different forms. Herein, the embodiments are provided to provide complete disclosure of the inventive concept and to provide thorough understanding of the inventive concept to those skilled in the art to which the inventive concept pertains, and the scope of the inventive concept should be limited only by the accompanying claims and equivalents thereof.

Terms used herein are only for description of embodiments and are not intended to limit the inventive concept. As used herein, the singular forms are intended to include the plural forms as well, unless context clearly indicates otherwise. It will be further understood that the terms "comprise" and/or "comprising" specify the presence of stated features, components, and/or operations, but do not preclude the presence or addition of one or more other features, components, and/or operations. In addition, identical numerals will denote identical components throughout the specification, and the meaning of "and/or" includes each mentioned item and every combination of mentioned items. It will be understood that, although the terms first, second, etc. may be used herein to describe various components, these components should not be limited by these terms. These terms are only used to distinguish one component from another component. Thus, a first component discussed below could be termed a second component without departing from the teachings of the inventive concept.

Unless otherwise defined, all terms (including technical and scientific terms) used herein have the same meaning as commonly understood by those skilled in the art to which the inventive concept pertains. It will be further understood that terms, such as those defined in commonly used dictionaries, should not be interpreted in an idealized or overly formal sense unless expressly so defined herein.

Spatially relative terms, such as "beneath", "below", "lower", "above", "upper" and the like, may be used herein for ease of description to describe one component or feature's relationship to another component(s) or feature(s) as illustrated in the figures. It will be understood that the spatially relative terms are intended to encompass different orientations of the device in use or operation in addition to the orientation depicted in the figures. For example, if the device in the figures is turned over, components described as "below" or "beneath" other components or features would then be oriented "above" the other components or features. Thus, the exemplary term "below" can encompass both an orientation of above and below. The device may be otherwise oriented (rotated 90 degrees or at other orientations) and the spatially relative descriptors used herein interpreted accordingly.

Hereinafter, embodiments of the inventive concept will be described in detail with reference to the accompanying drawings.

Figure 3:
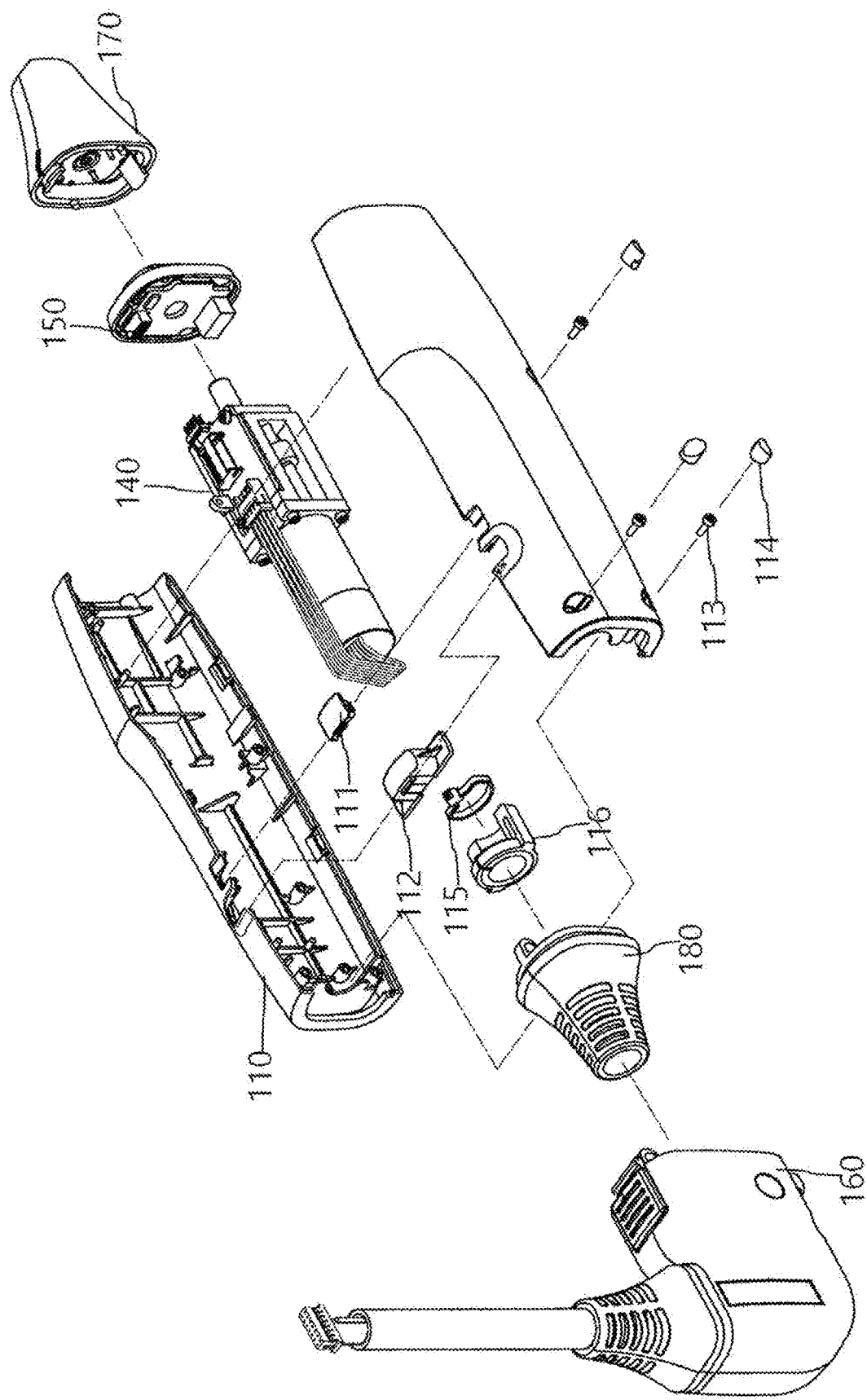
FIG. 3 is an exploded perspective view illustrating a skin treatment apparatus according to an embodiment of the inventive concept.
Figure 4:
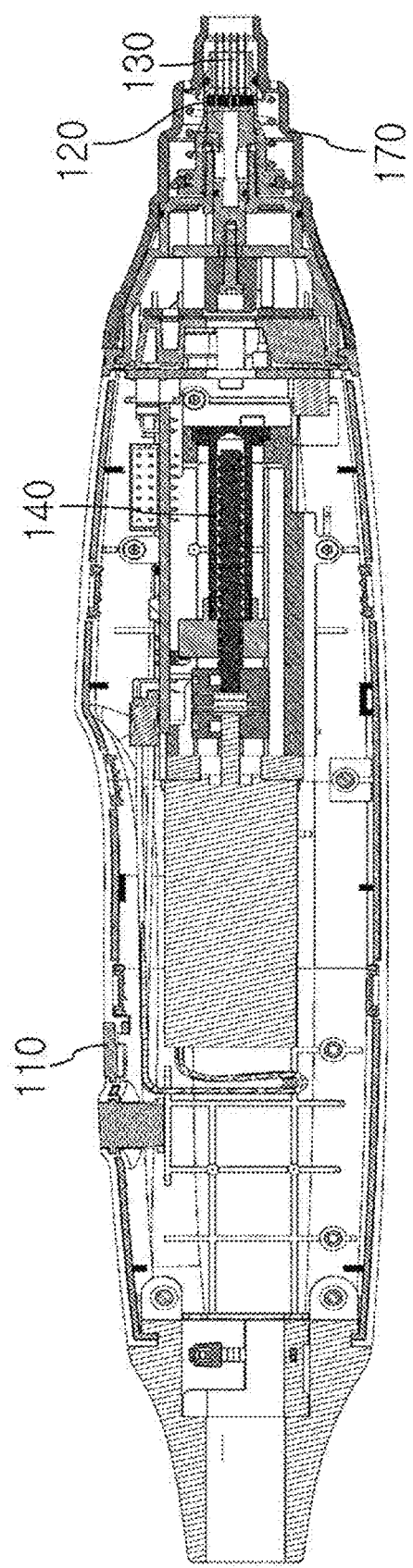
FIG. 4 is a sectional view illustrating the skin treatment apparatus according to an embodiment of the inventive concept.

FIG. 3 is an exploded perspective view illustrating a skin treatment apparatus according to an embodiment of the inventive concept, and FIG. 4 is a sectional view illustrating the skin treatment apparatus according to an embodiment of the inventive concept.

As illustrated in FIGS. 3 and 4, the skin treatment apparatus according to an embodiment of the inventive concept may include a casing 110, a needle tip for application of current, an actuator 140, an electricity supply device 150, a connector 160, a cartridge 170, a connecting member 180, and a controller (not illustrated).

The casing 110 accommodates the actuator 140 and the electricity supply device 150. The cartridge 170 is coupled to one side of the casing 110 so as to be replaceable, and the connector 160 is coupled to an opposite side of the casing 110 through the connecting member 180.

The casing 110 may be divided into a left casing and a right casing. The left casing and the right casing may be detachably coupled together through bolts 113, inserts 114, a first coupling member 111, and a second coupling member 112. The bolts 113 may fasten the left casing and the right casing. The inserts 114 may surround heads of the bolts 113. One end and an opposite end of the first coupling member 111 may be fit into the left casing 110 and the right casing 110, respectively. One end and an opposite end of the second coupling member 112 may be fit into the left casing 110 and the right casing 110, respectively.

The opposite side of the casing 110 may be coupled with the connecting member 180 through a third coupling member 115 and a fourth coupling member 116. The insides of the third coupling member 115, the fourth coupling member 116, and the connecting member 180 may be connected to allow electrical cables of the connector 160 to pass therethrough.

The needle tip for application of current may transfer electrical energy generated by current applied by the electricity supply device 150 to a target region of skin to remove damaged collagen or elastic fibers in the target region of the skin and facilitate forming new collagen or elastic fibers. The needle tip may include a needle fixing part 120 and a plurality of needles 130.

The needle fixing part 120 may be disposed inside the cartridge 170 and may be reciprocally moved into or out of the cartridge 170 by the actuator 140. The needle fixing part 120 may fix the plurality of needles 130. Accordingly, when the needle fixing part 120 is reciprocally moved into or out of the cartridge 170 by the actuator 140, the plurality of needles 130 may also be reciprocally moved into or out of the cartridge 170 by the actuator 140.

For example, on one surface of the needle fixing part 120, the plurality of needles 130 may be fixedly arranged to have at least one of one or more rows and one or more columns.

Furthermore, the needle fixing part 120 may have, in the one surface thereof, a plurality of through-holes through which the plurality of needles 130 are inserted.

The plurality of needles 130 are inserted into the skin to transfer the electrical energy generated by the current applied by the electricity supply device 150 to the target region of the skin.

Specifically, while the surface of the skin is brought into close contact with a contact surface of the cartridge 170, the plurality of needles 130 are moved out of the cartridge 170 together with the needle fixing part 120 and inserted into the skin by the actuator 140 and transfer the electrical energy, which is generated by the current applied by the electricity supply device 150, to the target region of the skin.

Meanwhile, the plurality of needles 130 inserted into the skin have to be rapidly pulled out to prevent a risk of accident and reduce a pain in the skin. Accordingly, the controller, which will be described below, may operate the actuator 40 to rapidly pull out the plurality of needles 130 inserted into the skin.

The plurality of needles 130 may be implemented in a bipolar type including both needles 130 having a positive (+) polarity and needles 130 having a negative (−) polarity. In the bipolar type, the current applied to the needles 130 having the positive (+) polarity reflux the needles 130 having the negative (−) polarity. As a result, an energy transfer region, to which electrical energy is transferred, may be formed between active regions 132a or 132b of the plurality of needles 130. Meanwhile, the positive (+) polarity may be a positive electrode, and the negative (−) polarity may be a negative electrode.

The needles 130 may have an empty space inside and may be formed of a conductive material, such as metal or silicone, or a non-conductive material. In a case where the needles 130 are formed of a non-conductive material, the needles 130 may be formed in a structure in which the non-conductive material is plated with a conductive material.

A partial region of each of the needles 130 that includes a tip end may be coated with an insulating material, and the tip end may be formed in a sharp structure. The insulating material coating may be implemented with a parylene coating, a Teflon coating, or a ceramic coating. The insulating material-coated partial region (e.g., a first insulated region or a second insulated region) of the needle 130 that includes the tip end will be described below.

In addition, the non-insulating material-coated active regions of the needles 130 are electromagnetically energized. Accordingly, the current applied to the active regions of the needles 130 having the positive (+) polarity reflux the active regions of the needles 130 having the negative (−) polarity. As a result, electrical energy may be transferred to between the active regions of the plurality of needles 130. The active regions will be described below.

The actuator 140 is installed inside the casing 110 and reciprocally moves the needle fixing part 120 and the plurality of needles 130 into or out of the cartridge 170. The actuator 140 may be driven by any one of an electromagnetic force caused by an electrical signal, hydraulic pressure, pneumatic pressure, and a solenoid valve.

The electricity supply device 150 is installed inside the casing 110 and applies current to the plurality of needles 130. The current applied to the plurality of needles 130 by the electricity supply device 150 may RF current, and the strength of the current applied to the plurality of needles 130 by the electricity supply device 150 may be controlled by the controller.

The connector 160 may be electrically connected to an external power supply and may have the electrical cables that electrically connect the actuator 140, the controller, and the electricity supply device 150 with the external power supply.

The connecting member 180 connects the connector 160 and the opposite side of the casing 110, and the electrical cables of the connector 160 pass through the connecting member 180.

The cartridge 170 may be a housing in which the needle tip for application of current is received. Hereinafter, the cartridge 170 is defined as the housing in which the needle tip for application of current is received.

The cartridge 170 may have a contact surface brought into close contact with the surface of the skin into which the plurality of needles 130 are inserted, and may be detachably coupled to the one side of the casing 110. As described above, the cartridge 170 may contain the plurality of needles 130 fixed to the needle fixing part 120 that is reciprocally moved into or out of the cartridge 170 by the actuator 140.

The contact surface of the cartridge 170 may be formed to be a flat surface. Accordingly, the surface of the skin brought into close contact with the contact surface of the cartridge 170 may be in a flat state. Due to this, the plurality of needles 130 may be inserted into the surface of the skin in the flat state, and the depths by which the plurality of needles 130 are inserted into the skin may be the same. As a result, only a region up to a specific depth of the skin may be uniformly disposed between the plurality of needles 130, and thus electrical energy transferred to between the plurality of needles 130 may be transferred only to the specific depth of the skin.

The cartridge 170 may have, in the contact surface thereof, a plurality of through-holes through which the needles 130 pass. Accordingly, the needles 130 may protrude outward from the cartridge 170 through the plurality of through-holes.

The contact surface of the cartridge 170 may be formed of rubber or silicone so as to be easily brought into close contact with the surface of the skin. Furthermore, the contact surface of the cartridge 170 may be formed in a circular or polygonal shape.

Meanwhile, the cartridge 170 may have a first space formed between the contact surface of the cartridge 170, which is brought into close contact with the surface of the skin, and the needle fixing part 120, and negative pressure may be formed in the first space before the plurality of needles 130 are inserted into the skin. The negative pressure may be formed by the controller when the surface of the skin is brought into close contact with the contact surface of the cartridge 170, or when the needle fixing part 120 and the plurality of needles 130 are moved out of the cartridge 170 by the actuator 140. Furthermore, the negative pressure may be formed by a pump (not illustrated) that suctions air in the first space, and the pump may be installed inside the casing 110.

Accordingly, when the surface of the skin is brought into close contact with the contact surface of the cartridge 170, the negative pressure is formed in the first space, and the surface of the skin sticks to the contact surface of the cartridge 170. As a result, the surface of the skin brought into close contact with the contact surface of the cartridge 170 may be in a flat state.

The controller serves to control the actuator 140 and the electricity supply device 150.

For example, the controller may control the distance by which the actuator 140 reciprocates the needle fixing part 120 and the plurality of needles 130 such that the plurality of needles 130 are inserted into the target region of the skin in the state in which the surface of the skin is brought into close contact with the contact surface of the cartridge 170.

In addition, the controller may operate the electricity supply device 150 such that electrical energy is transferred to the skin through the plurality of needles 130 in the state in which the plurality of needles 130 are inserted into the skin.

Meanwhile, when the plurality of needles 130 are inserted into the skin in the state in which the surface of the skin is brought into close contact with the contact surface of the cartridge 170, the surface of the skin brought into close contact with the contact surface of the cartridge 170 may be deflected by pressure applied to the surface of the skin by the plurality of needles 130. To compensate for the deflection, the needles 130 fixed to the needle fixing part 120 may preferably have different lengths.

For example, when the plurality of needles 130 are inserted into the skin, needles 130 disposed on the center of the needle fixing part 120 among the plurality of needles 130 may be inserted in a more sagged state than needles 130 disposed on the periphery of the needle fixing part 120.

To compensate for the deflection, the needles 130 disposed on the center of the needle fixing part 120 may have a greater length than the needles 130 disposed on the periphery of the needle fixing part 120. That is, the needles 130 disposed on the center of the needle fixing part 120 further protrude from the needle fixing part 120 beyond the needles 130 disposed on the periphery of the needle fixing part 120.

Figure 5:
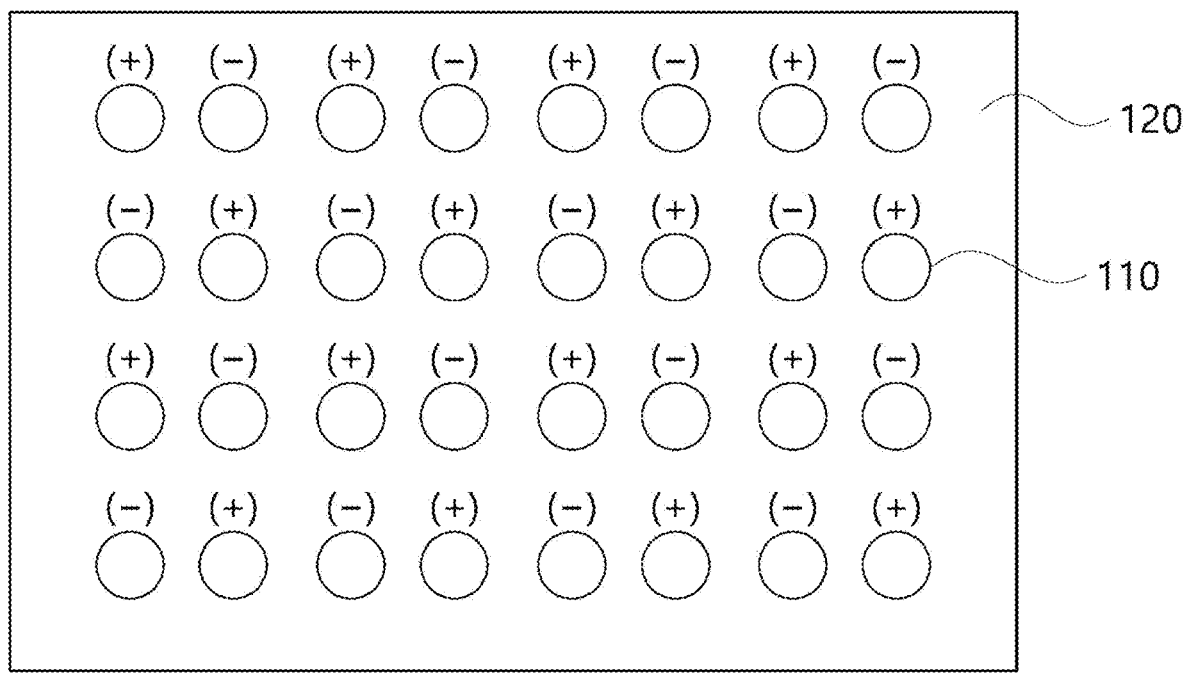
FIG. 5 is a plan view illustrating a state in which needles are disposed on a needle fixing part of a needle tip for application of current according to an embodiment of the inventive concept (bipolar type)
Figure 6:
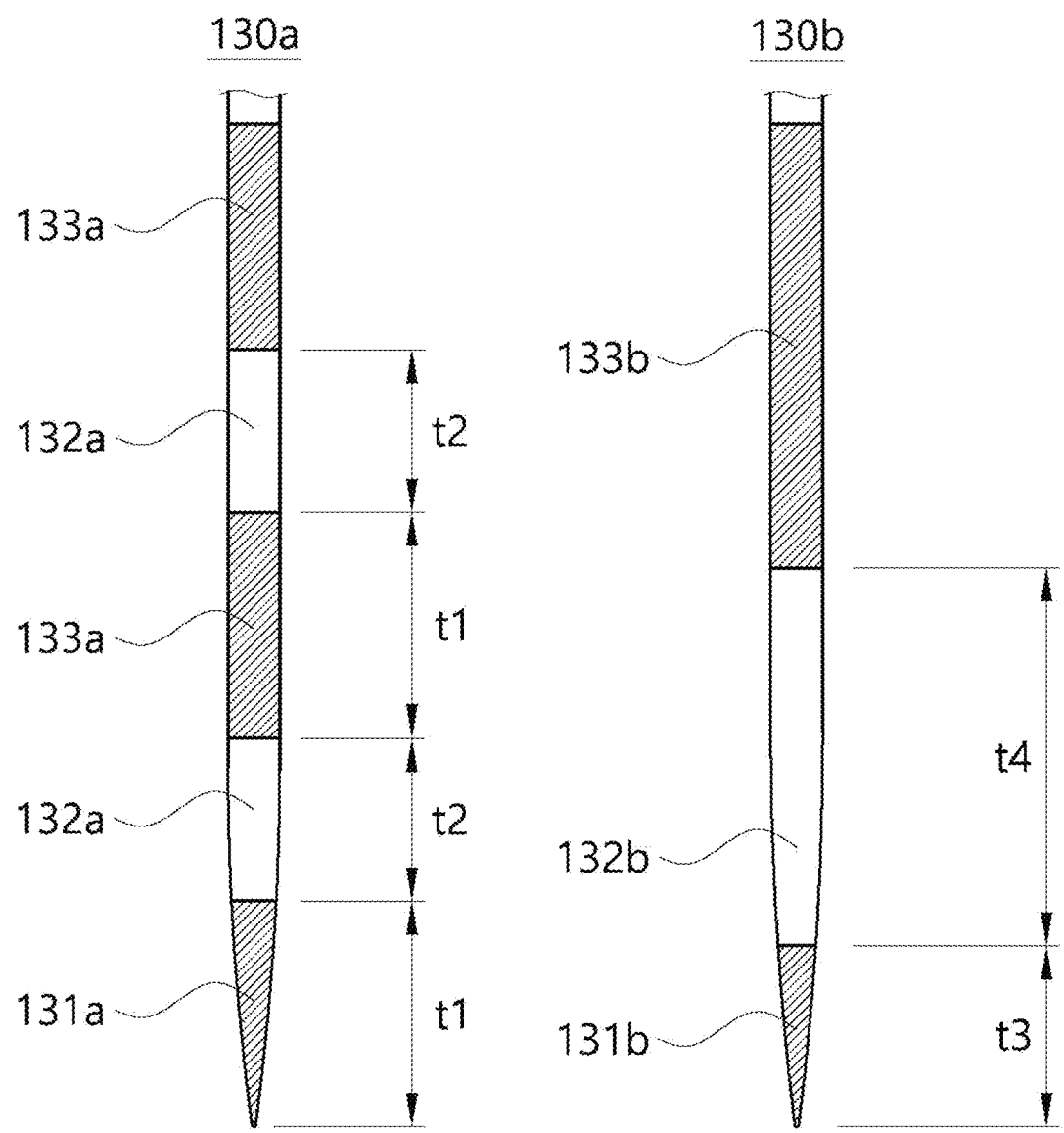
FIG. 6 is a schematic view illustrating needles according to an embodiment of the inventive concept.
Figure 7:
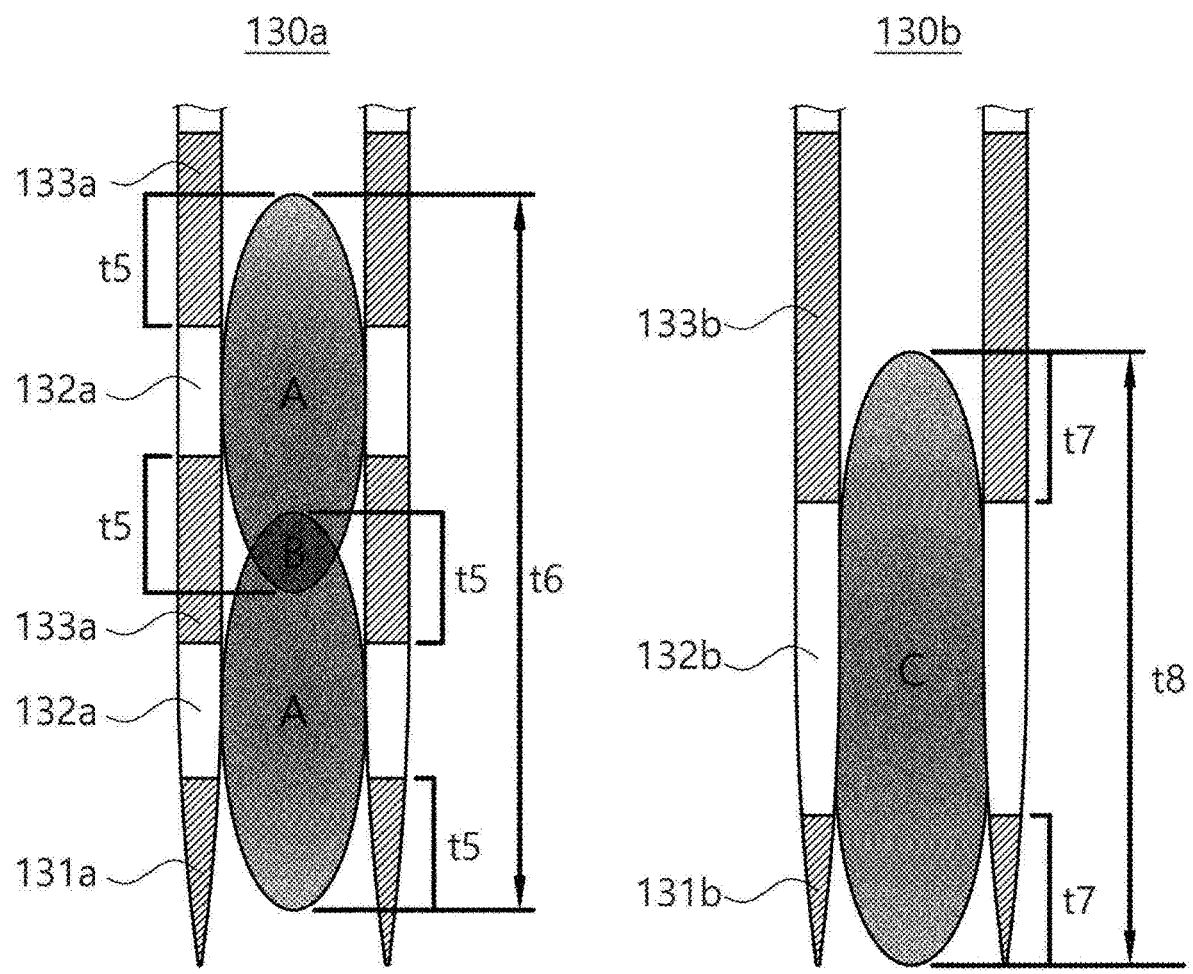
FIG. 7 is a schematic view illustrating energy transfer regions of the needle tip for application of current according to an embodiment of the inventive concept (bipolar type)
Figure 8A:
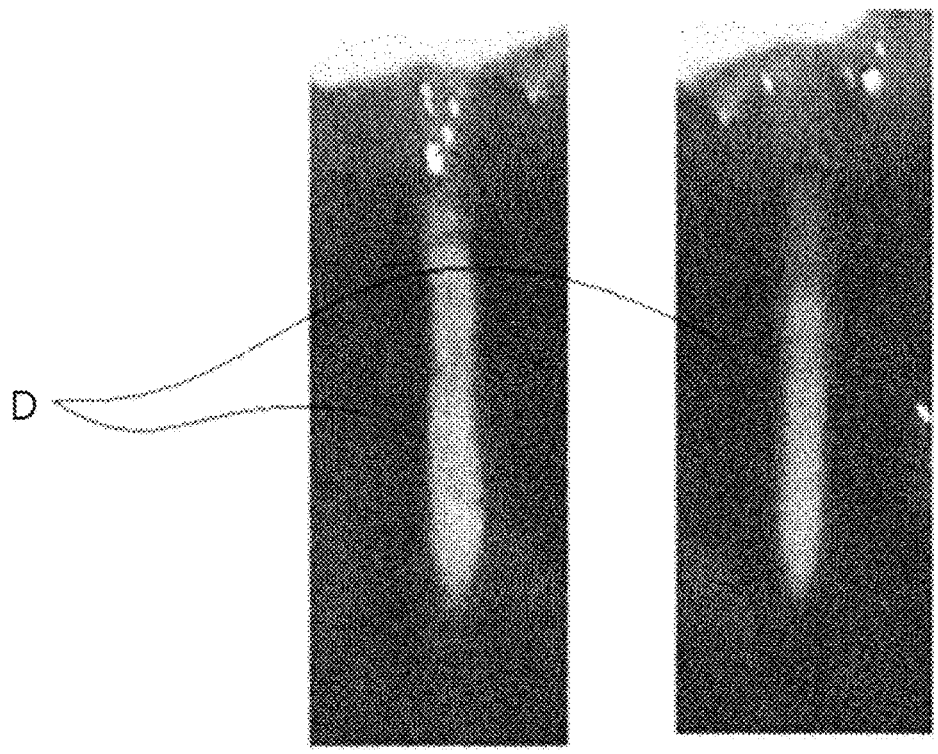
FIGS. 8A and 8B are views illustrating electrical energy transfer effects of needles according to an embodiment of the inventive concept (bipolar type)
Figure 8B:
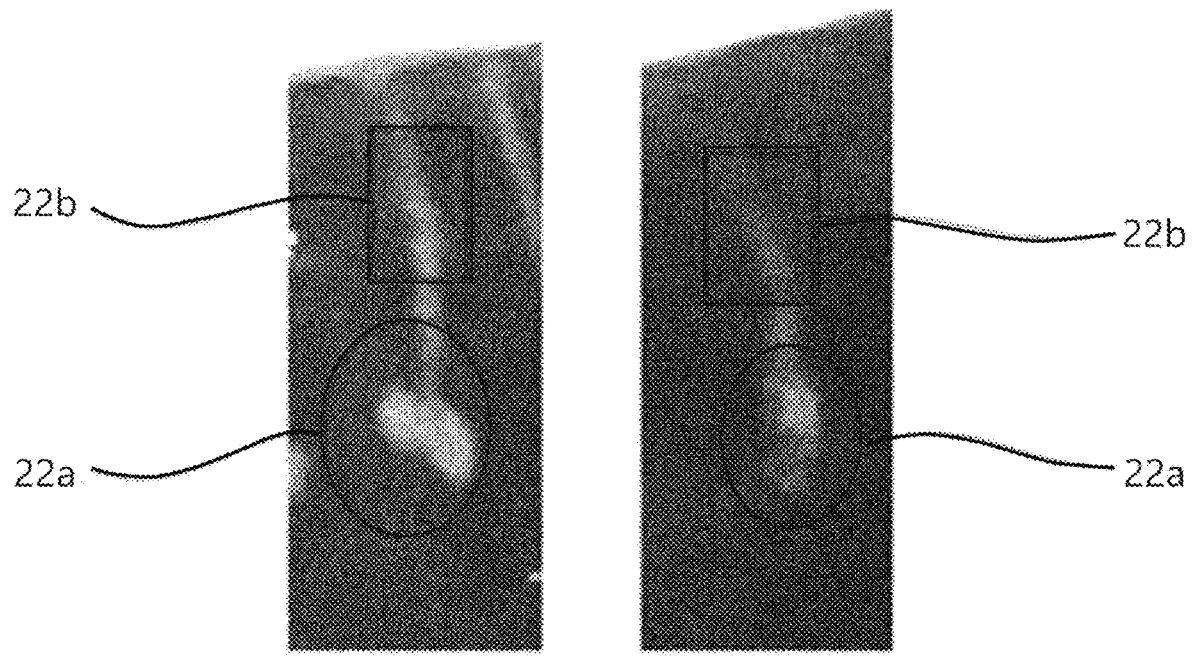
Figure 9A:
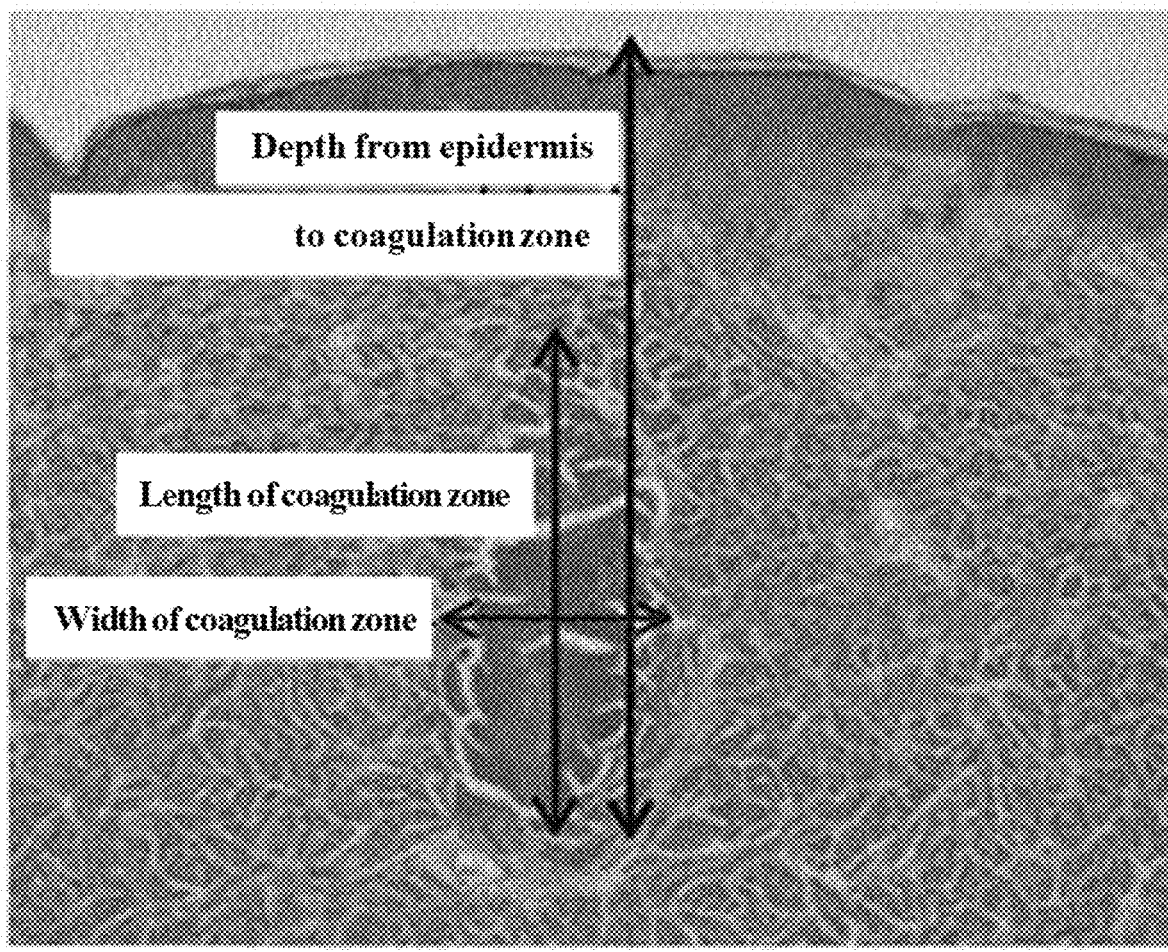
FIGS. 9A to 9D illustrate a graph depicting the depth from the outermost layer of skin to a coagulation zone formed in the skin through a plurality of first needles, a graph depicting the length of the coagulation zone, and a graph depicting the width of the coagulation zone according to an embodiment of the inventive concept.
Figure 9B:
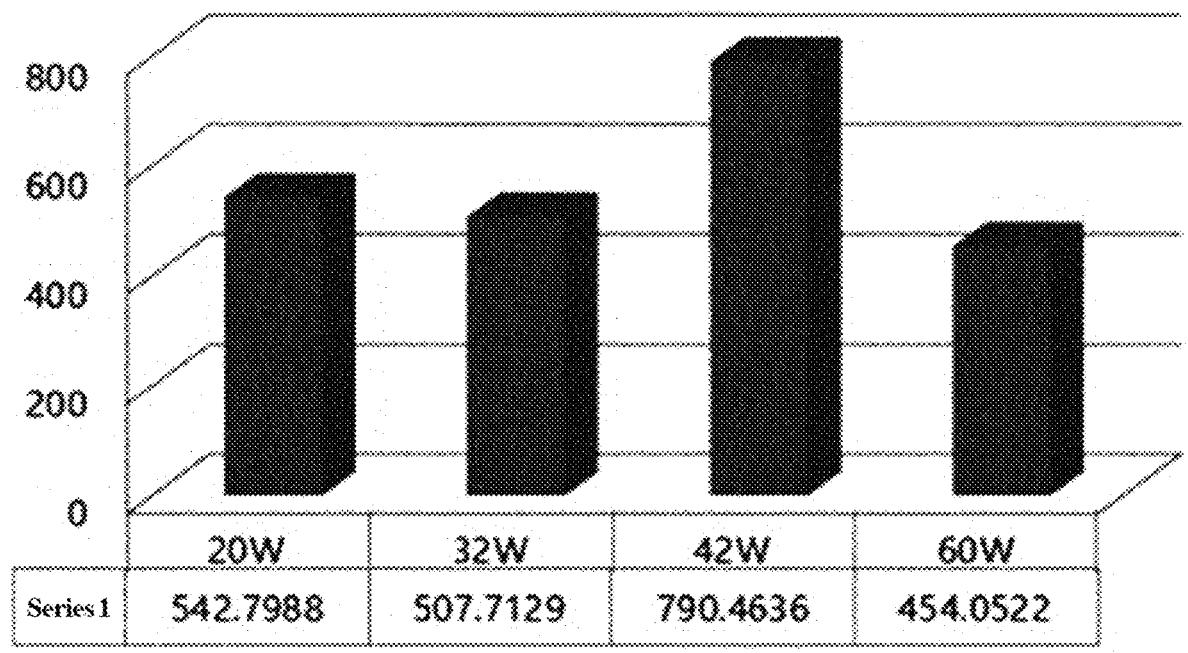
Figure 9C:
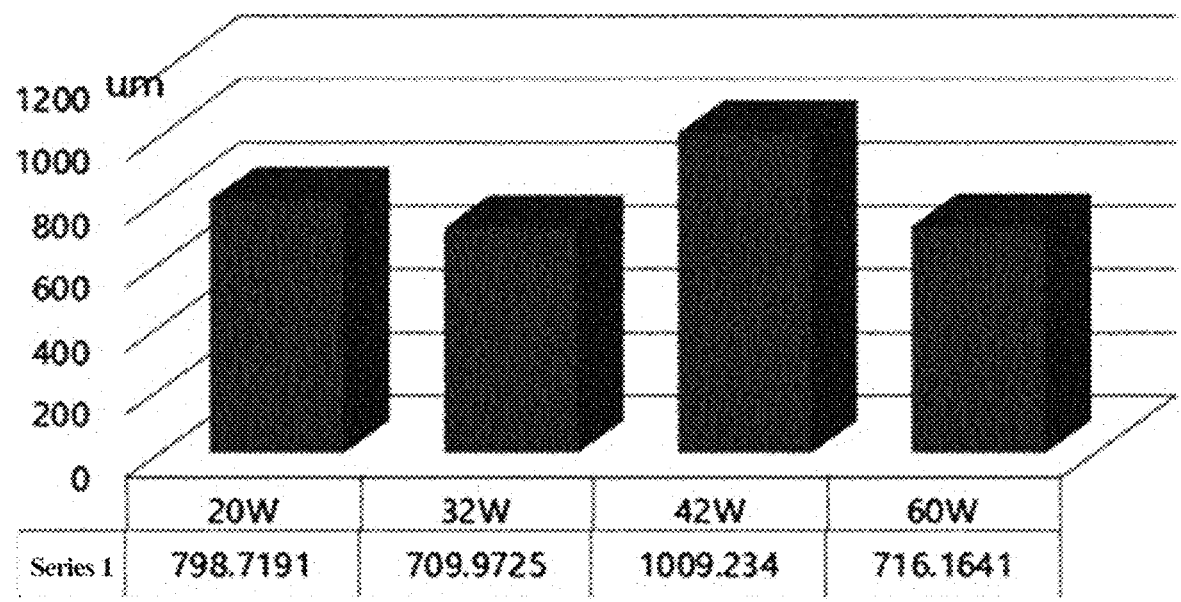
Figure 9D:
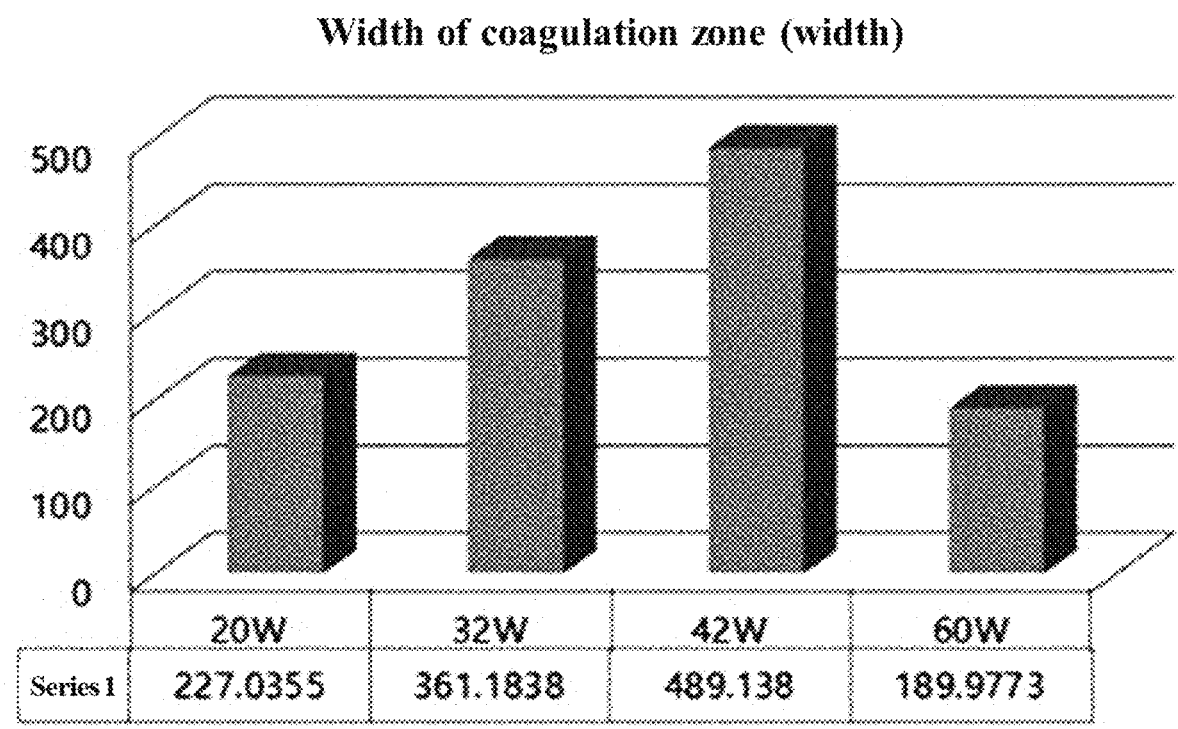

FIG. 5 is a plan view illustrating a state in which needles are disposed on the needle fixing part of the needle tip for application of current according to an embodiment of the inventive concept (bipolar type). FIG. 6 is a schematic view illustrating needles according to an embodiment of the inventive concept. FIG. 7 is a schematic view illustrating energy transfer regions of the needle tip for application of current according to an embodiment of the inventive concept (bipolar type). FIGS. 8A and 8B are views illustrating electrical energy transfer effects of needles according to an embodiment of the inventive concept (bipolar type).

Referring to FIG. 5, the needle tip for application of current according to an embodiment of the inventive concept serves to transfer, to the target region of the skin, electrical energy generated by current (that is, RF current) applied by the external power supply. The needle tip may include the needle fixing part 120 and the plurality of needles 130.

The needle fixing part 120 is the same as the needle fixing part 120 of the skin treatment apparatus described above. Therefore, detailed description thereof will be omitted.

The plurality of needles 130, after inserted into the skin, transfer the electrical energy generated by the current applied by the external power supply to the target region of the skin. Here, the insertion of the plurality of needles 130 into the skin may be performed by the actuator and the controller of the skin treatment apparatus described above.

The plurality of needles 130 may be fixedly disposed on one surface of the needle fixing part 120.

For example, on the one surface of the needle fixing part 120, the plurality of needles 130 may be fixedly arranged to have at least one of one or more rows and one or more columns.

In each row and column, needles 130 adjacent to each other among the plurality of needles 130 may output different polarities, and the plurality of needles 130 may be implemented in a bipolar type including both needles 130 having a positive (+) polarity and needles 130 having a negative (−) polarity.

Referring to FIG. 5, the plurality of needles 130 may alternately output a positive (+) polarity and a negative (−) polarity for each row of the needles 130 and may alternately output a positive (+) polarity and a negative (−) polarity for each column of the needles 130.

Accordingly, two needles 130 adjacent to each other along a row or column include a needle 130 having a positive (+) polarity and a needle 130 having a negative (−) polarity.

When current is applied to the plurality of needles 130 of a bipolar type, the current applied to the needles 130 having the positive (+) polarity reflux the needles 130 having the negative (−) polarity, or the current applied to the needles 130 having the negative (−) polarity reflux the needles 130 having the positive (+) polarity. As a result, damaged regions may be formed at specific depths of the skin through energy transfer regions A and C where electrical energy is transferred to between the active regions 132a and 132b of the plurality of needles 130.

The inventive concept may form the damaged regions at the specific depths of the skin through the energy transfer regions A and C where the electrical energy is transferred to between the active regions 132a and 132b of the plurality of needles 130.

Meanwhile, at least one of two or more needles 130 adjacent to one needle 130 may have the same polarity as the one needle 130.

Referring to FIGS. 6 and 7, each of the plurality of needles 130 may have a first insulated region 131a or 131b formed at a tip end thereof, and at least one active region 132a or 132b and at least one second insulated region 133a or 133b formed in the remaining portion thereof.

The first insulated region 131a or 131b may be formed by coating the tip end of the needle 130 with an insulating material.

The active region 132a or 132b is a predetermined exposed region other than the tip end of the needle 130. Specifically, the active region 132a or 132b is exposed by not coating a predetermined region other than the tip end of the needle 130 with an insulating material. The active region 132a or 132b is electromagnetically energized by current applied to the needle 130.

Meanwhile, when the plurality of needles 130 of a bipolar type are inserted into the skin and current is applied to the plurality of needles 130, the current applied to the active regions 132a and 132b of the needles 130 having the positive (+) polarity reflux the active regions 132a and 132b of the needles 130 having the negative (−) polarity, and the energy transfer regions A and C where electrical energy is transferred to between the active regions 132a and 132b of the plurality of needles 130 are formed. Damaged regions D having a uniform thickness are formed in the skin through the energy transfer regions A and C.

Because the tip ends of the plurality of needles 130 are insulated by the first insulated regions 131a and 131b, electrical energy is not transferred to the skin from the tip ends of the plurality of needles 130 on which the RF current is concentrated. Accordingly, unlike existing needles (that is, needles, tip ends of which are not coated with an insulating material), the plurality of needles 130 may prevent a damaged region having a bell shape from being generated in the skin adjacent to the tip ends of the plurality of needles 130.

Referring to FIG. 8A, it can be seen that laceration and a damaged region having a bell shape, which are caused by the existing needles (that is, needles, tip ends of which are not coated with an insulating material), are not generated in the skin adjacent to the tip ends of the plurality of needles 130.

Furthermore, as the energy transfer regions A and C of the plurality of needles 130 are generated in the skin adjacent to the active regions 132a and 132b of sidewalls of the plurality of needles 130, the damaged regions D are preferentially generated in the skin adjacent to the sidewalls of the plurality of needles 130.

In contrast, referring to FIG. 8B, when RF current is concentrated on tip ends of the plurality of existing needles of a bipolar type (that is, needles, tip ends of which are not coated with an insulating material) due to the nature of the RF current, excessive electrical energy is transferred from the tip ends to the skin, and therefore first damaged regions 22a having a bell shape and laceration are generated in the skin adjacent to the tip ends.

Furthermore, as energy transfer regions of the plurality of existing needles to which electrical energy is transferred are preferentially generated in the skin adjacent to the tip ends of the plurality of existing needles and are generated later in the skin adjacent to sidewalls of the plurality of existing needles, the first damaged regions 22a are preferentially generated in the skin adjacent to the tip ends of the plurality of existing needles, and thereafter second damaged regions 22b are generated in the skin adjacent to the sidewalls of the plurality of existing needles.

Therefore, even in a case where the second damaged regions 22b are desired to be preferentially generated in the skin adjacent to the sidewalls of the plurality of existing needles, the first damaged regions 22a are generated in the skin adjacent to the tip ends, and thereafter the second damaged regions 22b are generated in the skin adjacent to the sidewalls. Accordingly, unnecessary electrical energy is supplied, and treatment time is delayed.

Referring to FIGS. 6 and 7, the plurality of needles 130 may include a first needle 130a and a second needle 130b. Hereinafter, for convenience of description, the first needle 130a and the second needle 130b will be described as examples of the plurality of needles 130.

The first needle 130a may have the first insulated region 131a formed at the tip end thereof, and a plurality of active regions 132a and a plurality of second insulated regions 133a alternately formed in the remaining portion thereof. For example, the first needle 130a may have the single first insulated region 131, and two or more active regions 132a and two or more second insulated regions 133a alternately formed (refer to the left side of FIG. 6).

In a case where the plurality of needles 130 include only the first needles 130a, when the plurality of first needles 130a are inserted into the skin, the plurality of energy transfer regions A spaced apart from each other are formed between the plurality of first needles 130a, and electrical energy is supplied to a plurality of skin regions through the plurality of energy transfer regions A spaced apart from each other.

The second needle 130b may have the single first insulated region 131b, the single active region 132b, and the single second insulated region 133b. That is, the second needle 130b may have the first insulated region 131b formed at the tip end thereof, and the single active region 132b and the single second insulated region 133b formed along the lengthwise direction in the remaining portion thereof (refer to the right side of FIG. 6).

Referring to FIG. 7, as the plurality of needles 130 have one or more active regions 132a and 132b disposed at the same height, the energy transfer regions A and C formed between the active regions 132a and 132b of the needles 130 are disposed only at a specific depth of the skin when the plurality of needles 130 are inserted into the skin. Accordingly, electrical energy may be supplied to the specific depth of the skin through the energy transfer regions A and C disposed at the specific depth of the skin.

The active regions 132a and 132b of the needles 130 may be formed to have the same size. Specifically, the active regions 132a of the needles 130 may have the same length and thickness.

Meanwhile, the sizes (e.g., depths and widths) by which the energy transfer regions A and C are formed in the skin may be adjusted by adjusting the strength of current applied to the plurality of needles 130. The electricity supply device or the controller of the skin treatment apparatus described above may be used to adjust the strength of the current, and detailed description thereabout will be given in an experimental example that will be described below.

Referring to the left side of FIG. 7, in a case where the plurality of needles 130 are constituted by the plurality of first needles 130a having the plurality of active regions 132a spaced apart from each other and the plurality of energy transfer regions A are formed between the plurality of first needles 130a, electrical energy may be supplied to a plurality of skin regions through the plurality of energy transfer regions A when the plurality of first needles 130a are inserted into the skin.

However, according to the need of a user, it may be necessary to transfer electrical energy to between the energy transfer regions A.

To achieve this, the plurality of energy transfer regions A formed between the plurality of first needles 130a may be spread in the lengthwise direction by adjusting the strength of current applied to the plurality of first needles 130a within a specific numerical range. As a result, electrical energy may be transferred to between the plurality of energy transfer regions A.

In this case, the diameter of the first needle 130a may range from 0.23 mm to 0.27 mm, the length t1 of the first insulated region 131a of the first needle 130a may range from 0.28 mm to 0.32 mm, the length t1 of the active region 132a of the first needle 130a may range from 0.23 mm to 0.27 mm, the separation distance t2 between the active regions 132a of the first needles 130a (that is, the length of the second insulated region 133a located between the active regions 132a of the first needles 130a) may range from 0.28 mm to 0.32 mm, and the length of the second insulated region 133a located at the top of the first needle 130a is not specially limited. In addition, the gap between the plurality of first needles 130a may range from 1 mm to 2.4 mm. However, the inventive concept is not limited thereto.

The reason for the above-described numerical values will be described below in the experimental example.

Experimental Example

FIGS. 9A to 9D illustrate a graph depicting the depth from the outermost layer of skin to a coagulation zone formed in the skin through energy transfer regions formed between a plurality of first needles, a graph depicting the length of the coagulation zone, and a graph depicting the width of the coagulation zone according to an embodiment of the inventive concept.

The depth from the outermost layer of the skin to the coagulation zone formed in the skin through the two energy transfer regions A formed between the two active regions 132a of the plurality of first needles 130a and the length and width of the coagulation zone formed in the skin were measured after the plurality of first needles 130a constituted by the first insulated region 131a having the above-described numerical value and the second insulated region 133a interposed between the two active regions 132a having the above-described numerical value were inserted into the skin and current was applied to the plurality of first needles 130a.

Here, the strength of the current applied to the plurality of first needles 130a was adjusted to 20 W to 60 W. The electricity supply device or the controller of the skin treatment apparatus described above was used to adjust the strength of the current.

As a result, in the case where the current ranging from 20 W to 60 W was applied to the plurality of first needles 130a, the depth from the outermost layer of the skin to the coagulation zone (that is, the depth by which the energy transfer regions were formed in the skin) was adjusted to 0.71 mm to 1.00 mm. That is, it can be seen that the depth by which the energy transfer regions A were formed in the skin was adjusted by adjusting the strength of the current applied to the plurality of first needles 130a (refer to the graphs of FIGS. 9A and 9C that depict the depth from the outermost layer of the skin to the coagulation zone).

Furthermore, in the case where the current ranging from 20 W to 60 W was applied to the plurality of first needles 130a, the width of the coagulation zone (that is, the width by which the energy transfer regions were formed in the skin) was adjusted to 0.18 mm to 0.48 mm. That is, it can be seen that the width by which the energy transfer regions A were formed in the skin was adjusted by adjusting the strength of the current applied to the plurality of first needles 130a (refer to the graphs of FIGS. 9A and 9D that depict the width of the coagulation zone).

Moreover, in the case where the current ranging from 20 W to 50 W was applied to the plurality of first needles 130a, the maximum length obtained by adding the lengths of the two active regions 132a was 0.54 mm (that is, 0.27 mm×2), and the length of the coagulation zone formed in the skin through the two energy transfer regions A ranged from 0.542 mm to 0.790 mm.

That is, it can be seen that the length of the coagulation zone formed in the skin through the two energy transfer regions A was greater than the maximum length obtained by adding the lengths of the two active regions 132a. Accordingly, it can be seen that the two energy transfer regions A were spread in the lengthwise direction.

However, in the case where the current smaller than 20 W or greater than 50 W was applied to the plurality of first needles 130a, the two energy transfer regions were not spread in the lengthwise direction. Accordingly, the strength of current applied to the first needles 130a preferably ranges from 20 W to 50 W (refer to the graphs of FIGS. 9A and 9B that depict the length of the coagulation zone).

In addition, in the case where the strength of current applied to the plurality of first needles 130a was 42 W, the maximum length obtained by adding the lengths of the two active regions 132a and the second insulated region 133a was 0.74 mm (that is, 0.23 mm×2+0.28 mm), and the length of the coagulation zone formed in the skin through the two energy transfer regions A was 0.790 mm.

That is, it can be seen that the length of the coagulation zone formed in the skin through the two energy transfer regions A was greater than the maximum length obtained by adding the lengths of the two active regions 132a and the second insulated region 133a. Accordingly, it can be seen that the two energy transfer regions A had the overlapping region B having the length of 0.05 mm (0.790 mm-0.74 mm) (refer to FIG. 7 and the graphs of FIGS. 9A and 9B that depict the length of the coagulation zone).

The concept of the overlapping region B is illustrated on the left side of FIG. 7.

As described above, the plurality of energy transfer regions A spaced apart from each other in the lengthwise direction may be formed between the plurality of first needles 130a.

In the case where the strength of current applied to the plurality of first needles 130a is 42 W, the plurality of energy transfer regions A formed between the plurality of first needles 130a are spread along the lengthwise direction by more than half of the length of the second insulated region 133a. Accordingly, the overlapping region B is formed in the plurality of energy transfer regions A.

The length t5 by which the plurality of energy transfer regions A are spread in the lengthwise direction may range from 0.23 mm to 0.25 mm, and the total length t6 of two energy transfer regions A adjacent to each other among the plurality of energy transfer regions A spread as described above may range from 1.25 mm to 1.32 mm.

Referring to the right side of FIG. 7, for example, in the case where the plurality of needles 130 are constituted by the plurality of second needles 130b, an energy transfer region C may be formed between the active regions 132b of the plurality of second needles 130b. When the plurality of second needles 130b are inserted into the skin, electrical energy may be supplied to a single skin region through the energy transfer region C.

Referring to the left side of FIG. 6 and the right side of FIG. 7, for example, the diameter of the second needle 130b may range from 0.23 mm to 0.27 mm, the length t3 of the first insulated region 131b of the second needle 130b may range from 0.18 mm to 0.22 mm, the length t4 of the active region 132b of the second needle 130b may range from 0.48 mm to 0.52 mm, and the length of the second insulated region 133b located at the top of the second needle 130b is not specially limited.

In addition, the gap between the second needles 130b may range from 1 mm to 2.4 mm. However, the inventive concept is not limited thereto.

Meanwhile, in the case where the strength of current applied to the plurality of second needles 130b ranges from 20 W to 50 W, the energy transfer region C formed between the active regions 132b of the plurality of second needles 130b was spread in the lengthwise direction. The length by which the energy transfer region C is spread may range from 0.23 mm to 0.25 mm, and the total length of the energy transfer region C may range from 0.98 mm to 1.02 mm.

Accordingly, as the first insulated regions are formed at the tip ends of the needles, the needle tip for application of current according the embodiment of the inventive concept may prevent electrical energy concentrated on the tip ends of the needles from being transferred to the skin to generate damaged regions having a bell shape.

Furthermore, as the active regions of the plurality of needles are disposed at the same height, the needle tip for application of current according to the embodiment of the inventive concept may supply electrical energy only to a specific depth of the skin through the energy transfer regions formed between the active regions of the needles.

For example, the plurality of needles 130 may be implemented in a mono-polar type in which the plurality of needles 130 are connected to one or more RF sources (e.g., the electricity supply device of the skin treatment apparatus), the plurality of needles 130 arranged in at least one of the longitudinal direction and the lateral direction alternately output the same polarity separately or in combination thereof, and a ground electrode having an opposite polarity is provided. For example, the plurality of needles 130 may all output a positive (+) polarity, and the ground electrode may be implemented to have a negative (−) polarity. Alternatively, the plurality of needles 130 may all output a negative (−) polarity, and the ground electrode may be implemented to have a positive (+) polarity.

Figure 10A:
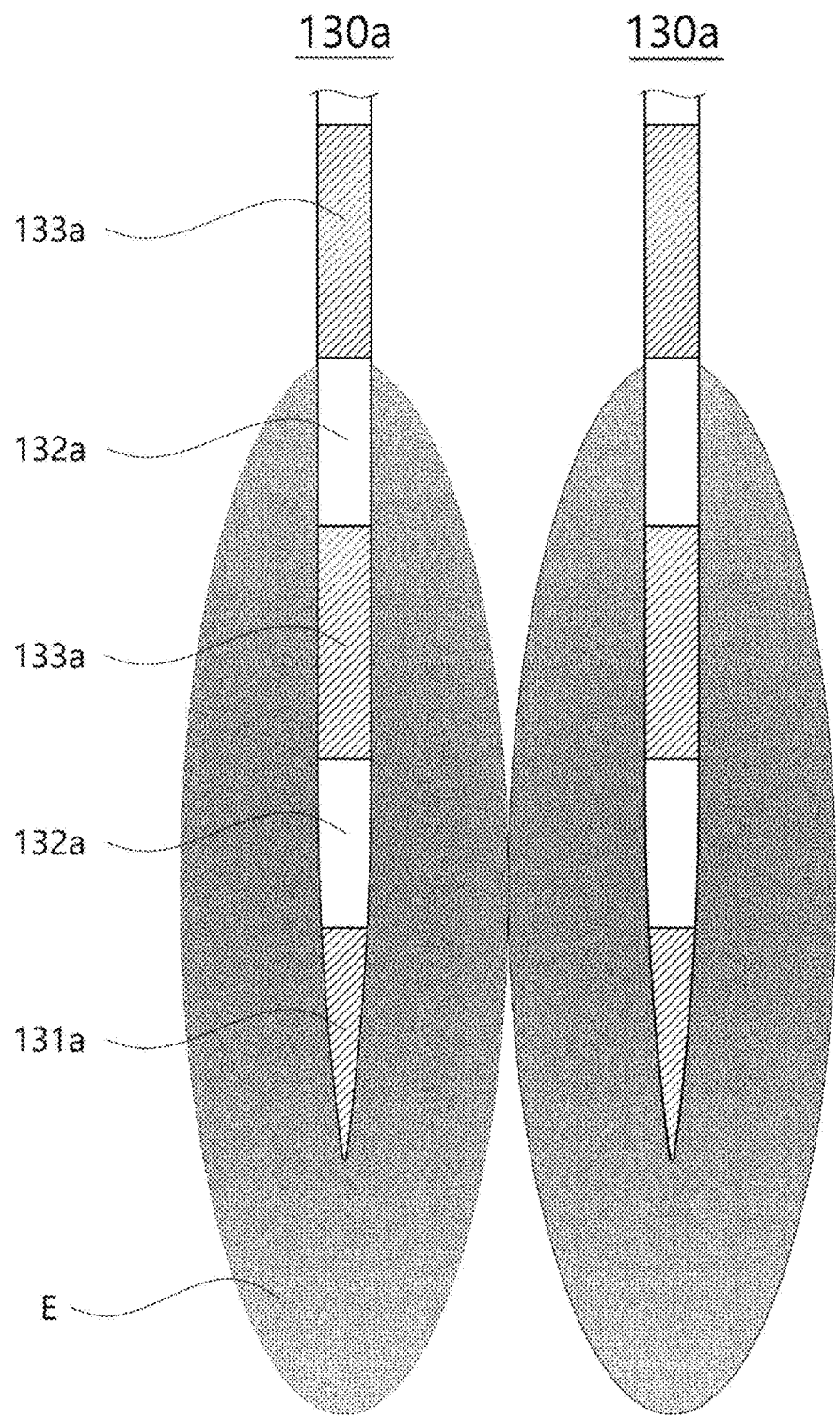
FIGS. 10A and 10B are views illustrating electrical energy transfer effects of needles according to an embodiment of the inventive concept (mono-polar type)
Figure 10B:
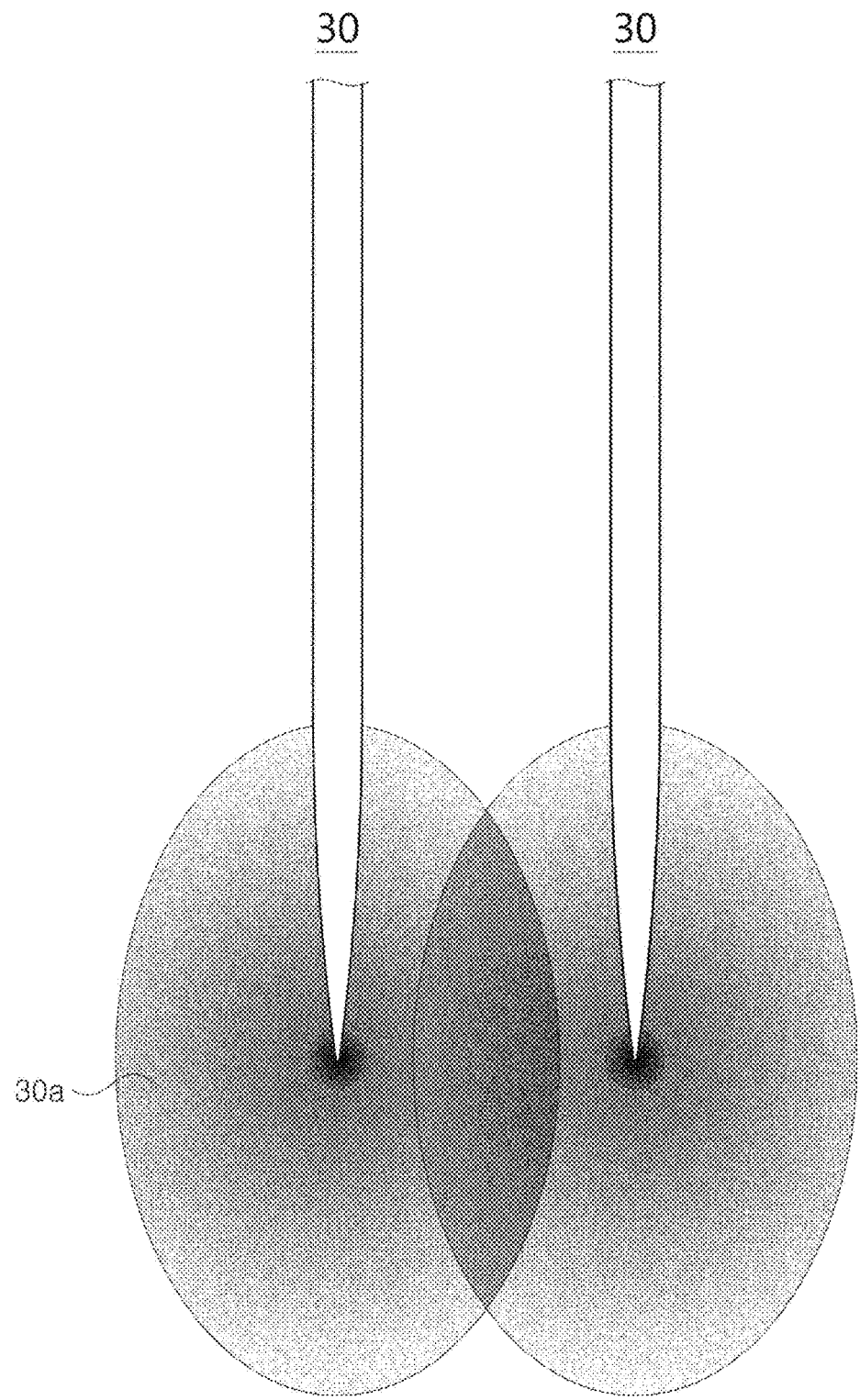

FIGS. 10A and 10B are views illustrating electrical energy transfer effects of needles according to an embodiment of the inventive concept (mono-polar type).

Hereinafter, for convenience of description, needles 130 of a mono-polar type will be described based on first needles 130a of a mono-polar type. Second needles 130b of a mono-polar type have the same function and effect as the first needles 130a of a mono-polar type.

Referring to FIG. 10A, when the first needles 130a of a mono-polar type are inserted into skin and RF current is applied to the first needles 130a, the RF current is concentrated on tip ends of the first needles 130a due to the nature of the RF current. As the tip ends of the first needles 130a are insulated and active regions 132a of sidewalls of the first needles 130a are exposed, the RF current applied to the first needles 130a circulates from the active regions 132a of the sidewalls of the first needles 130a to a ground electrode disposed at a non-target point (e.g., outside the skin).

As a result, energy transfer regions E to which electrical energy is transferred from the active regions 132a of the sidewalls of the first needles 130a are formed over a wide range, and a wide skin region may be treated through the energy transfer regions E.

That is, the skin treatment range of the first needles 130a is improved.

Because electrical energy is not transferred from the tip ends of the first needles 130a, on which the RF current is concentrated, to the skin even though the first needles 130a remain inserted into the skin and the RF current is continually applied, a damaged region having a bell shape and laceration may be prevented from being generated in the skin adjacent to the tip ends of the first needles.

Furthermore, as the energy transfer regions E of the first needles 130a are generated from skin regions adjacent to the active regions 132a of the sidewalls of the first needles 130a, damaged regions are preferentially generated from the skin regions adjacent to the sidewalls of the first needles 130a.

In contrast, referring to FIG. 10B, when existing needles 30 of a mono-polar type (that is, needles, the tip ends of which are not coated with an insulating material) are inserted into skin and RF current is applied to the existing needles 30, the RF current is concentrated on tip ends of the existing needles 30 due to the nature of the RF current. As the tip ends of the existing needles 30 are exposed, the current applied to the existing needles 30 circulates to a ground electrode disposed at a non-target point (e.g., outside the skin) with respect to the tip ends of the existing needles 30.

As a result, energy transfer regions 30a to which electrical energy is transferred with respect to the tip ends of the existing needles 30 are formed over a narrow range, and a narrow skin region may be treated through the energy transfer regions 30a.

That is, the skin treatment range of the existing needles 30 is limited.

Because excessive electrical energy is transferred from the tip ends of the existing needles 30, on which the RF current is concentrated, to the skin when the existing needles 30 remain inserted into the skin and the RF current is continually applied, a damaged region having a bell shape and laceration are generated in skin regions adjacent to the tip ends of the existing needles 30.

Furthermore, as the energy transfer regions 30a of the existing needles 30 are preferentially generated in the skin regions adjacent to the tip ends of the existing needles 30 and thereafter generated in skin regions adjacent to sidewalls of the existing needles 30, first damaged regions are preferentially generated in the skin regions adjacent to the tip ends, and thereafter second damaged regions are generated in the skin regions adjacent to the sidewalls.

Accordingly, even in a case where the second damaged regions are desired to be preferentially generated in the skin regions adjacent to the sidewalls of the existing needles 30, the second damaged regions are generated in the skin regions adjacent to the sidewalls after the first damaged regions are generated in the skin regions adjacent to the tip ends. As a result, unnecessary electrical energy is supplied, and treatment time is delayed.

Meanwhile, the plurality of needles 130 of a mono-polar type may include the first needles 130a and the second needles 130b alternately arranged along a row and a column. The first needles 130a may be grouped into a group of first needles 130a, and the second needles 130b may be grouped into a group of second needles 130b.

For example, based on FIG. 5, the needles 130 represented by (+) may be grouped into the group of first needles 130a, and the needles 130 represented by (−) may be grouped into the group of second needles 130b.

RF current may be alternately applied to the group of first needles 130a and the group of second needles 130b.

For example, the group of first needles 130a and the group of second needles 130b may be connected in parallel to the same RF source, and RF current may be alternately applied to the group of first needles 130a and the group of second needles 130b by switching the same RF source.

In another example, the group of first needles 130a and the group of second needles 130b may be separately connected to different RF sources, and as the different RF sources apply RF current at different time, the RF current may be alternately applied to the group of first needles 130a and the group of second needles 130b.

When the RF current is applied to the group of first needles 130a and the group of second needles 130b at different time, a proximity effect occurring in the plurality of needles 130 of a mono-polar type that have the group of first needles 130a and the group of second needles 130b may be prevented.

Here, the proximity effect means that the RF current applied to the plurality of needles 130 of a mono-polar type flows through only a part of the plurality of needles 130 of a mono-polar type. For example, the proximity effect may mean that the RF current flows through only needles located at the periphery among the plurality of needles 130 of a mono-polar type, or may mean that the RF current flows through only needles located in the center among the plurality of needles 130 of a mono-polar type.

Figure 11:
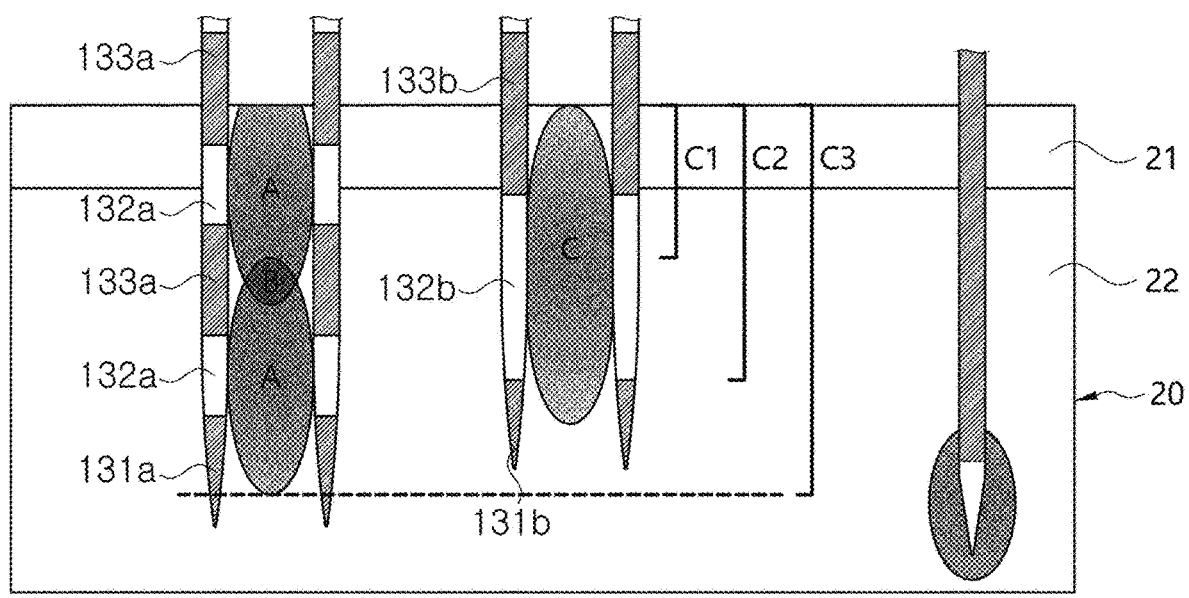
FIG. 11 is a schematic view illustrating energy transfer regions of a first needle and a second needle according to an embodiment of the inventive concept.

FIG. 11 is a schematic view illustrating energy transfer regions of a first needle and a second needle according to an embodiment of the inventive concept.

As illustrated in FIG. 11, the depth C1 of skin by which electrical energy needs to be transferred to treat freckles may be 0.5 mm or less, the depth C2 of skin by which electrical energy needs to be transferred for skin tone, skin texture, and skin tightening may be 1 mm or less, and the depth C3 of skin by which electrical energy needs to be transferred to treat hair follicles and rosacea may be 1.25 mm or less.

That is, because the depth of skin by which electrical energy needs to be transferred varies depending on treatment targets, the first needle 130a and the second needle 130b of the inventive concept may form energy transfer regions at different skin depths.

Furthermore, the first needle 130a may form an energy transfer region at a skin depth for treatment of freckles, skin ton, skin texture, skin tightening, hair follicles, and rosacea, and the second needle 130b may form an energy transfer region at a skin depth for treatment of freckles, skin tone, skin texture, and skin tightening.

Figure 12:
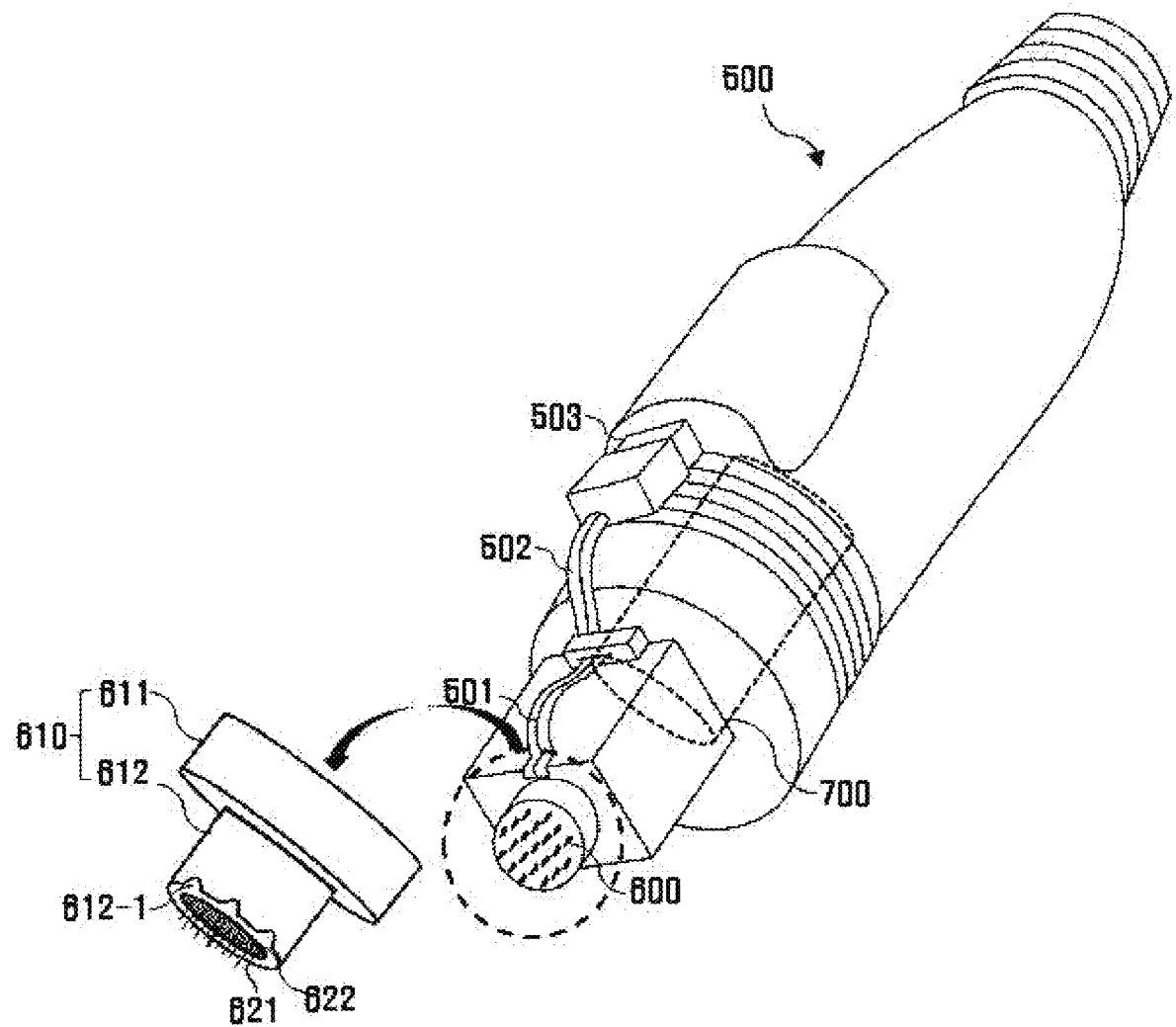
FIG. 12 is a perspective view illustrating a hand piece according to an embodiment of the inventive concept.
Figure 13:
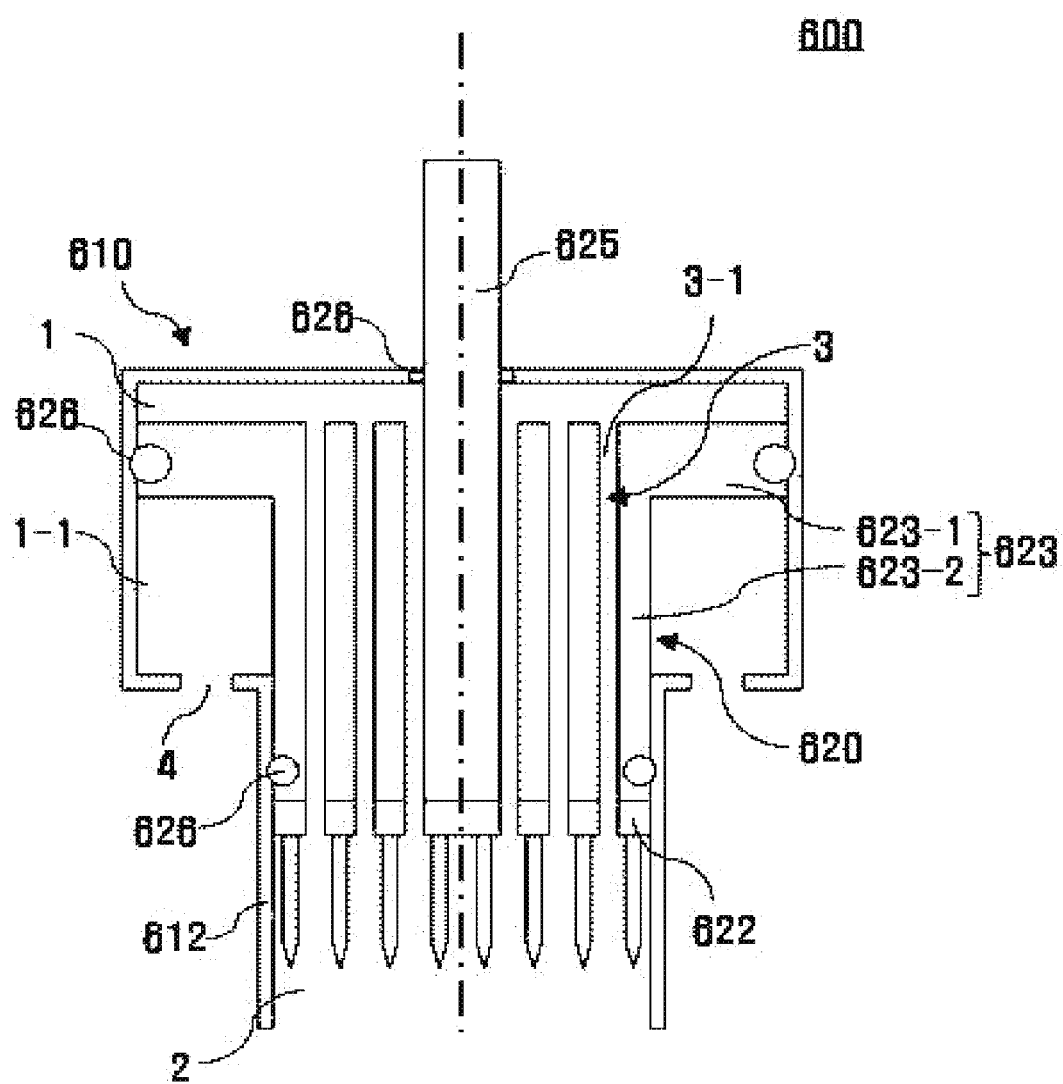
FIG. 13 is a sectional view illustrating a needle tip for application of current mounted on the hand piece according to an embodiment of the inventive concept.
Figure 14:
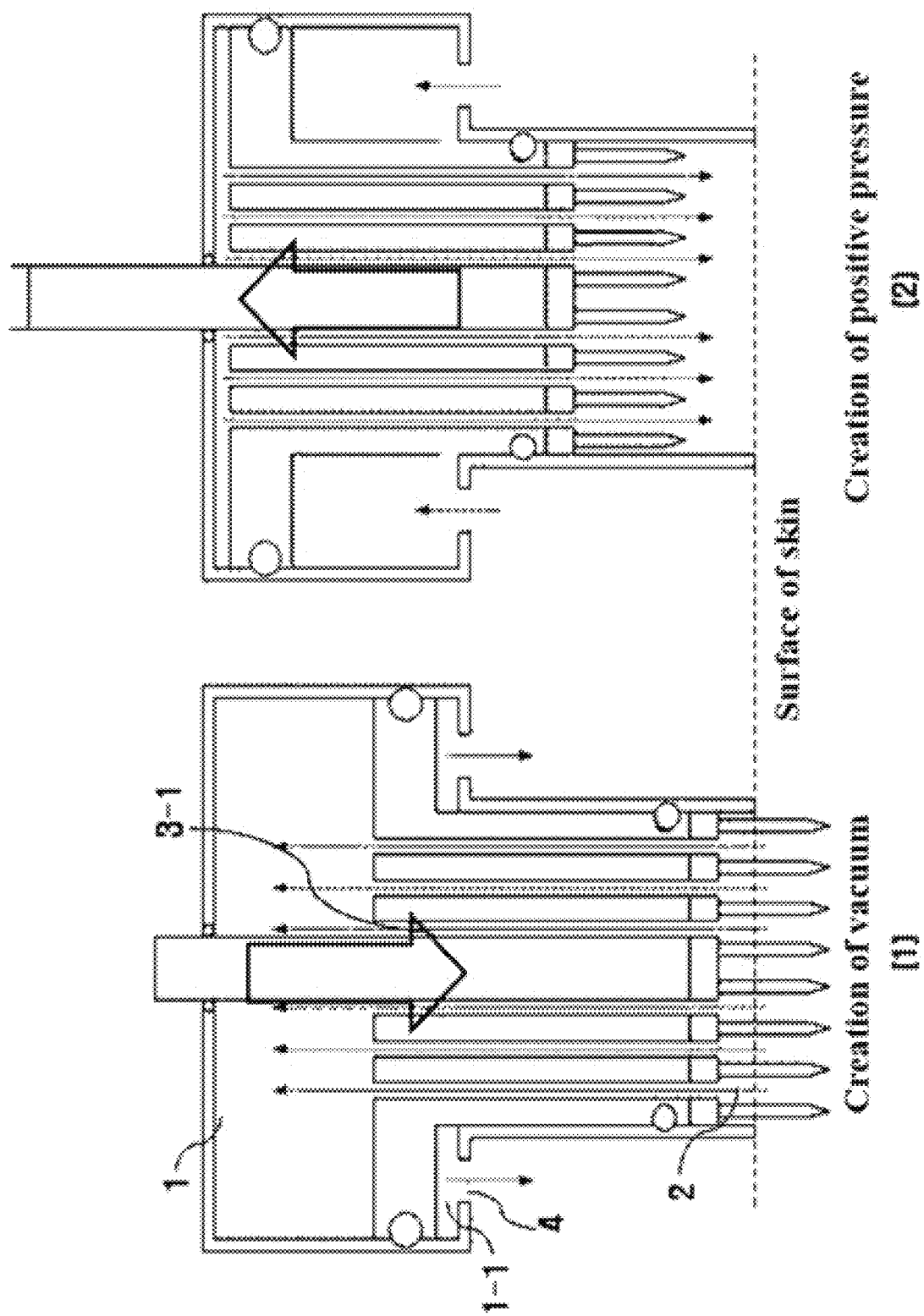
FIG. 14 is a sectional view illustrating a state in which a pumping effect occurs in the needle tip for application of current mounted on the hand piece according to an embodiment of the inventive concept.

FIG. 12 is a perspective view illustrating a hand piece according to an embodiment of the inventive concept. FIG. 13 is a sectional view illustrating a needle tip for application of current mounted on the hand piece according to an embodiment of the inventive concept. FIG. 14 is a sectional view illustrating a state in which a pumping effect occurs in the needle tip for application of current mounted on the hand piece according to an embodiment of the inventive concept.

As illustrated in FIGS. 12 to 14, the hand piece 500 may be included.

The hand piece 500 is a part that a doctor grasps. The doctor may change a target point (e.g., a portion of a face) by moving the hand piece 500 in a state of bringing the hand piece 500 into contact with the skin of a target person. The hand piece 500 may be connected to the skin treatment apparatus through a cable.

An actuator module 700 and a power supply module may be embedded in the hand piece 500. The cable may electrically connect the actuator module 700 and the power supply module, which are embedded in the hand piece 500, with an electronic control module embedded in the skin treatment apparatus. The needle tip 600 for application of current may be mounted on an end portion of the hand piece 500. In this case, the needle tip 600 for application of current may be mounted on the end portion of the hand piece 500 by being received in a cartridge that is mounted on the end portion of the hand piece 500 so as to be replaceable.

The hand piece 500 may include, on the exterior thereof, a first conductive member 501 that electrically connects a needle unit 620 of the needle tip 600 for application of current and the power supply module and a second conductive member 502 that is docked with a cable connector 503 and that electrically connects the power supply module and the cable. In this case, the first conductive member 501 and the second conductive member 502 may be manufactured in the form of a film. For example, the first conductive member 501 and the second conductive member 502 may be flexible printed circuit boards (FPCBs). Because the needle unit 620 of the needle tip 600 for application of current reciprocally moves (operates) as will be described below, the conductive line that electrically connects the needle unit 620 of the needle tip 600 for application of current and the power module and the conductive line that electrically connects the power module and the cable are provided on the exterior of the hand piece 500 such that the conductive lines are not brought into contact with the needle unit 620 during the reciprocation of the needle unit 620 of the needle tip 600 for application of current.

The needle tip 600 for application of current may be member that applies radio frequency (RF) to a deep skin portion at the target point. The needle tip 600 for application of current may be mounted on the end portion of the hand piece 500 so as to be removable. The needle tip 600 for application of current may include a cylinder 610 and the needle unit 620. The cylinder 610, which is a stator, may be mounted on the end portion of the hand piece 500 so as to be removable. The needle unit 620, which is a movable component (moving in the vertical direction), may include one or more needles 621 and may be inserted into the deep skin portion at the target point according to a predetermined period (an operating period of the actuator module). The needle unit 620 may apply radio frequency (RF) to the dermal layer of the skin as needed.

The cylinder 610 may have an empty space formed therein in the vertical direction. The needle unit 620 may be disposed in the interior space of the cylinder 610. The cylinder 610 may be open at the bottom, and a lower end portion of the cylinder 610 may be disposed on the surface of the skin at the target point. Accordingly, the open portion of the cylinder 610 may be closed by the surface of the skin at the target point.

The cylinder 610 may include a first cylinder 611 and a second cylinder 612. In this case, the first cylinder 611 may be located on an upper side, and the second cylinder 612 may be located on a lower side. A lower end of the first cylinder 611 and an upper end of the second cylinder 612 may be connected. The second cylinder 612 may be open at the bottom.

The needle unit 620 may be disposed in the first cylinder 611 and the second cylinder 612, and a connecting portion between the first cylinder 611 and the second cylinder 612 may be closed by the needle unit 620.

A connecting rod 625 of the needle unit 620 may pass through an upper surface of the first cylinder 611. In the first cylinder 611, a first space 1 and an available space 1-1 may be formed by a first plunger 623-1 of the needle unit 620. That is, the interior space of the first cylinder 611 may be closed in the vertical direction by the first plunger 623-1 of the needle unit 620 and may be divided into the first space 1 located on an upper side and the available space 1-1 located on a lower side.

To maintain the air-tightness of the first space 1 of the first cylinder 611, a gasket 626 may be disposed between the upper surface of the first cylinder 611 and the connecting rod 625 of the needle unit 620. Furthermore, a gasket 626 may be disposed between the inner circumferential surface of the first cylinder 611 and the outer circumferential surface of the first plunger 623-1 of the needle unit 620.

A lower end of the second cylinder 612 may be disposed on the surface of the skin at the target point. Accordingly, the open lower portion of the second cylinder 612 may be closed by the surface of the skin at the target point. In the second cylinder 612, an open-bottomed second space 2 may be formed by a second plunger 623-2 of the needle unit 620. The interior space of the second cylinder 612 may be closed in the vertical direction by the second plunger 623-2 of the needle unit 620. A holder 622 of the needle unit 620 and the second plunger 623-2 of the needle unit 620 may be disposed on an upper side of the interior space of the second cylinder 612, and the open-bottomed second space 2 may be located on a lower side of the interior space of the second cylinder 612.

One or more recesses 612-1 may be formed on a lower surface of the second cylinder 612 (refer to FIG. 3). The one or more recesses 612-1 of the second cylinder 612 may be formed from the outer circumferential surface of the second cylinder 612 to the inner circumferential surface of the second cylinder 612. That is, the one or more recesses 612-1 of the second cylinder 612 may be formed through the second cylinder 612. Furthermore, the one or more recesses 612-1 of the second cylinder 612 may be arranged to be spaced apart from each other along the periphery of the lower surface of the second cylinder 612. That is, the one or more recesses 612-1 of the second cylinder 612 may be formed to be spaced apart from each other in the circumferential direction.

Meanwhile, as described above, the open lower portion of the second space 2 may be closed by the surface of the skin at the target point. In this case, a gasket 626 may be disposed between the inner circumferential surface of the second cylinder 612 and the outer circumferential surface of the second plunger 623-2 of the needle unit 620 to maintain the air-tightness of the second space 2. Meanwhile, in the state of maintaining the air-tightness, only a lower end portion of the second space 2 is selectively connected with the outside by the one or more recesses 612-1 of the second cylinder 612 to raise a pumping effect.

The one or more needles 621 of the needle unit 620 may be disposed in the second space 2. Because the lower surface of the second space 2 is open as described above, the one or more needles 621 may pass through the open portion of the second space 2 and may penetrate the surface of the skin at the target point.

The cross-sectional area of the first cylinder 611 that is perpendicular to the vertical direction may be larger than the cross-sectional area of the second cylinder 612 that is perpendicular to the vertical direction. Accordingly, by reciprocation of a plunger 623 of the needle unit 620 in the vertical direction, a change in the volume of the first space 1 in the first cylinder 611 may be greater than a change in the volume of the second space 2 in the second cylinder 612.

The cylinder 610 may further include a seat 613 (refer to FIG. 11). The seat 613 may be located in the second space 2. The seat 613 may be disposed to be downwardly inclined toward the inside from the inner circumferential surface of the second cylinder 612. The seat 613 may have a ring shape and may be disposed along the inner circumferential surface of the second cylinder 612. In this case, likewise to the form of a valve seat, the seat 613 of the inventive concept may be disposed around the one or more needles 621 of the needle unit 620. That is, the seat 613 may cover the periphery of the one or more needles 621 of the needle unit 620.

An outer end portion of the seat 613 may be a fixed end, and an inner end portion of the seat 613 may be a free end. Accordingly, the angle by which the seat 613 is downwardly inclined may be varied by a flow of air around the seat 613. To improve the variation of the inclined angle, the seat 613 may be formed of an elastic material.

The outer end portion of the seat 613 may be disposed in a higher position than the one or more recesses 612-1 of the second cylinder 612. As a result, the inclination angle of the seat 613 may be varied depending on a flow of air flowing through the one or more recesses 612-1 of the second cylinder 612. The seat 613 may interact with the one or more recesses 612-1 of the second cylinder 612 to raise the pumping effect that will be described below.

The needle unit 620 may be disposed in the cylinder 610. The needle unit 620 may be reciprocated in the vertical direction by the actuator module 700. That is, the needle unit 620 may be disposed in the first cylinder 611 and the second cylinder 612 and may perform reciprocating motion, like a piston. In addition, the plunger 623 may partition the interior spaces of the first cylinder 611 and the second cylinder 612 and may change the volumes of the interior spaces of the first cylinder 611 and the second cylinder 612.

The needle unit 620 may be repeatedly (periodically) inserted into the skin at the target point by performing reciprocating motion in the vertical direction. In addition, the needle unit 620 may generate radio frequency in the deep skin portion at the target point, and collagen and elastic fibers damaged by thermal energy caused by the radio frequency may be regenerated over time to increase skin elasticity.

The needle unit 620 may include the one or more needles 621, the holder 622, the plunger 623, and the connecting rod 625. The needles 621 may be the needles 130 described above, and the holder 622 may be the needle fixing part 120 described above.

The one or more needles 621 may be alternately inserted into and pulled out of the skin while reciprocating together with the plunger 623. Radio frequency may be applied to the one or more needles 621 to generate thermal energy in the deep skin portion at the target point.

Without being limited thereto, however, electrical energy and ultrasonic waves in various wavelength bands, in addition to the radio frequency, may be applied to the one or more needles 621. In addition, as described above, electrical energy or ultrasonic waves may not be applied to the one or more needles 621.

In the case where electrical energy such as radio frequency is applied to the one or more needles 621, the one or more needles 621 may be electrically connected with the power supply module and may be supplied with power. To achieve this, the one or more needles 621 may be electrically connected with the power supply module through the first conductive member 501 described above.

Meanwhile, the one or more needles 621 may be an electrode unit of a bipolar type in which a plurality of electrodes have two polarities and radio frequency is generated between adjacent electrodes, or the one or more needles 621 may be an electrode unit of a mono-polar type in which a plurality of electrodes all have the same polarity. In the case where the one or more needles 621 are of a mono-polar type, a ground electrode module (not illustrated) that circulates radio frequency generated from the one or more needles 621 may be additionally provided.

The one or more needles 621 may be supported by the holder 622. The one or more needles 621 may extend downward from the holder 622. The one or more needles 621 may be disposed in the second space 2 of the second cylinder 612.

The one or more needles 621 may be reciprocated in the vertical direction by a driving force of the actuator module 700. At the bottom dead point of the needle unit 620, lower end portions of the one or more needles 621 may be disposed in the deep skin portion at the target point, and at the top dead point of the needle unit 620, the lower end portions of the one or more needles 621 may be disposed above the surface of the skin.

Accordingly, the one or more needles 621 may be repeatedly inserted into the deep skin portion at the target point. In this case, the one or more needles 621 may protrude downward through the open lower portion of the second space 2 in the second cylinder 612 and thereafter may retract upward. Meanwhile, the depth by which the one or more needles 621 are inserted into the skin may be about 2.1 mm.

The holder 622 may be a member that supports the one or more needles 621. Likewise to the one or more needles 621, the holder 622 may be disposed in the second space 2 of the second cylinder 612. Furthermore, the holder 622 may be disposed on a lower surface of the second plunger 623-2 and may be coupled with the second plunger 623-2. In addition, the holder 622 may be omitted in some cases. In this case, the one or more needles 621 may be directly disposed on the plunger 623.

The plunger 623 may form the first space 1 and the second space 2 in the cylinder 610 while reciprocating in the vertical direction. Furthermore, a first channel 3 that connects the first space 1 and the second space 2 may be formed in the plunger 623.

A change in the volume of the first space 1 by the reciprocation of the plunger 623 is greater than a change in the volume of the second space 2 by the reciprocation of the plunger 623. Therefore, when the plunger moves downward, gas in the second space 2 may move into the first space 1 through the first channel 3, and when the plunger moves upward, the gas in the first space 1 may move into the second space 2 through the first channel 3.

Accordingly, when the plunger 623 moves downward, the one or more needles 621 may be inserted into the skin, and a negative pressure state may be formed in the second space 2 (the pressure may be decreased), and when the plunger 623 moves upward, the one or more needles 621 may be pulled out of the skin, and a positive pressure state may be formed in the second space 2 (the pressure may be increased).

The plunger 623 may include the first plunger 623-1 and the second plunger 623-2. The first plunger 623-1 may be disposed in the interior space of the first cylinder 611. The first plunger 623-1 may close the interior space of the first cylinder 611 in the vertical direction to form the first space 1 located on the upper side of the first cylinder 611 and the available space 1-1 located on the lower side of the first cylinder 611.

The first plunger 623-1 may be reciprocated in the vertical direction by a driving force of the actuator module 700. When the first plunger 623-1 moves downward, the volume of the first space 1 may be increased, and the volume of the available space 1-1 may be decreased (refer to (1) of FIG. 14). When the first plunger 623-1 moves upward, the volume of the first space 1 may be decreased, and the volume of the available space 1-1 may be increased (refer to (2) of FIG. 14).

The second plunger 623-2 may be located in the interior space of the second cylinder 612. The second plunger 623-2 may close the interior space of the second cylinder 612 in the vertical direction to form the second space 2 in the second cylinder 612.

The second plunger 623-2 may be reciprocated in the vertical direction by a driving force of the actuator module 700. When the second plunger 623-2 moves downward, the volume of the second space 2 may be decreased (refer to (1) of FIG. 5). When the second plunger 623-2 moves upward, the volume of the second space 2 may be increased.

The first channel 3 that connects the first space 1 and the second space 2 may be formed in the first plunger 623-1 and the second plunger 623-2. In this case, the first channel 3 formed in the first plunger 623-1 and the second plunger 623-2 may be at least one flow passages 3-1 formed through the first plunger 623-1 and the second plunger 623-2 (or, formed in the first plunger and the second plunger) in the vertical direction.

The connecting rod 625 may be disposed above the first plunger 623-1. The connecting rod 625 may be moved in the vertical direction by a driving force of the actuator module 700. The connecting rod 625 may be connected with the actuator module 700 and the first plunger 623-1 and may perform a function of transferring the driving force of the actuator module 700 to the first plunger 623-1.

Hereinafter, an operation (a pumping effect) of the needle tip 600 for application of current will be described with reference to FIG. 14. When the skin treatment apparatus of the inventive concept is operated, the needle unit 620 may be repeatedly inserted into the skin at the target point while performing reciprocating motion in the vertical direction (the up/down direction) (in a case where radio frequency is applied, thermal energy is generated in the deep skin portion). Meanwhile, a medicine may be applied to the surface of the skin at the target point to alleviate a pain caused by the insertion of the needle unit 620 and facilitate regeneration of a wound.

When the needle unit 620 moves downward, the volume of the first space 1 may be increased, and the volume of the second space 2 may be decreased. In this case, due to the difference between the cross-sectional areas of the first and second spaces 1 and 2 perpendicular to the vertical direction, a change in the volume of the first space 1 may be greater than a change in the volume of the second space 2. That is, the increase in the volume of the first space 1 may be greater than the decrease in the volume of the second space 2. Meanwhile, because the first space 1 and the second space 2 are connected by the first channel 3, gas in the second space 2 may move into the first space 1 through the first channel 3 (refer to (1) of FIG. 11, a movement by a pressure difference caused by the volume change). Accordingly, the second space 2 may be in a negative pressure state (pressure decrease; in contrast, the first space is in a positive pressure state) and may suction the surface of the skin at the target point to make the height of the surface of the skin at the target point uniform. As a result, the one or more needles 621 may be inserted to a uniform depth (an effect of inserting the needles 621 to an equal depth, because the plurality of needles all irradiate radio frequency at a depth (a preset depth) that meets a medical design condition).

When the needle unit 620 moves upward, the volume of the first space 1 may be decreased, and the volume of the second space 2 may be increased. In this case, due to the difference between the cross-sectional areas of the first and second spaces 1 and 2 perpendicular to the vertical direction, a change in the volume of the first space 1 may be greater than a change in the volume of the second space 2. That is, the decrease in the volume of the first space 1 may be greater than the increase in the volume of the second space 2. Meanwhile, because the first space 1 and the second space 2 are connected by the first channel 3, the gas in the first space 1 may move into the second space 2 through the first channel 3 (refer to (2) of FIG. 5, a movement by a pressure difference caused by the volume change). As a result, the second space 2 may be in a positive pressure state (pressure increase; in contrast, the first space is in a negative pressure state) and may inject the medicine, which is applied to the surface of the skin at the target point, deep into the skin (a hole formed by inserting and pulling out the needle electrode) (an effect of injecting the medicine deep into the skin).

Meanwhile, a second channel 4 that connects the available space 1-1 and the outside may be formed in the first cylinder 611. The second channel 4 may prevent the pressure of gas in the available space 1-1 from hampering reciprocation of the first plunger 623-1 in the vertical direction. That is, when the needle unit 620 moves downward, the second channel 4 may release air in the available space 101 to the outside to remove a resistive force.

In an embodiment, a needle of the inventive concept may be manufactured as follows. Silicone having a thickness by which an active region corresponding to a non-insulated region is to be formed may be prepared. A needle may be coupled to a cartridge. The needle may be inserted into the silicone to a location where the active region of the needle is desired to be formed. A first insulated region and a second insulated region may be formed by spraying an insulating material in a state in which the needle is inserted into the silicone. Meanwhile, the needle may be finally assembled after manufactured such that a partial region is not insulated, or the needle may be insulated by being inserted into a silicone layer after manufactured.

Specifically, in a case of manufacturing a needle tip for application of current that includes the same number of active regions in the same specific positions, non-insulated needles are fixed to a cartridge, and the needles are inserted into silicone having a thickness corresponding to active region ranges. At this time, to simultaneously dispose the needles at the same depth, a silicone pad having a specific thickness may be pulled in opposite directions so as not to sag when the needles are inserted. Furthermore, in a case of forming the active regions in the same positions of the needles, the needles are inserted in a state in which the silicone pad having a thickness corresponding to the active region ranges is maintained by the distance between the active regions. Thereafter, the needles are insulated in a state in which the silicone is disposed in a position where the active regions are desired to be formed. Accordingly, the needles may have the active regions formed in the same positions.

Here, the silicone may be replaced by various materials through which needles are disposed in desired positions and that enable active regions to be formed within a desired thickness range. For example, a flexible material such as silicone or rubber may be used.

A method for manufacturing a needle tip for application of current according to an embodiment of the inventive concept includes preparing silicone having a thickness by which an active region corresponding to a non-insulated region is to be formed, coupling a plurality of needles to a needle fixing part, inserting the plurality of needles into the silicone up to locations of the plurality of needles where the active region is desired to be formed, and forming a tip end and an insulated region by spraying an insulating material in a state in which the plurality of needles are inserted into the silicone.

As described above, the active regions of the plurality of needles of the needle tip for application of current are disposed at the same height. Accordingly, the needle tip for application of current may supply electrical energy only to a specific depth of skin through the energy transfer regions formed between the active regions of the needles.

In addition, the tip ends of the needles are insulated. Accordingly, the needle tip for application of current may prevent excessive electrical energy concentrated on the tip ends of the needles from being transferred to skin.

Effects of the inventive concept are not limited to the aforementioned effects, and any other effects not mentioned herein will be clearly understood from the following description by those skilled in the art to which the inventive concept pertains.

While the inventive concept has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

What is claimed is:
1. A needle tip for application of current, the needle tip comprising:
 a needle fixing part; and
 a plurality of needles disposed on one surface of the needle fixing part, wherein a tip end of each of the plurality of needles is configured to be a first insulated region, wherein current is configured to be applied to the plurality of needles, and wherein the first insulated region is coated with an insulating material.

2. The needle tip of claim 1, wherein remaining portion of each of the plurality of needles is configured to be at least one active region and at least one second insulated region.

3. The needle tip of claim 2, wherein the active region is configured to be exposed and electromagnetically energized, and wherein the second insulated region are coated with an insulating material.

4. The needle tip of claim 3, wherein the plurality of needles include at least one first needle disposed at the center of the needle fixing part and at least one second needle disposed at an edge of the needle fixing part, and wherein the at least one first needle has a greater than the at least one second needle length.

5. The needle tip of claim 3, wherein needles adjacent to each other among the plurality of needles are configured to output different polarities or the same polarity, and wherein the at least one active region of each of the plurality of needles is disposed at the same height, and electrical energy is configured to be supplied to a specific depth of skin through an energy transfer region formed between the active regions of the plurality of needles.

6. The needle tip of claim 3, wherein the active regions of the plurality of needles have the same size.

7. The needle tip of claim 5, wherein the size by which the energy transfer region is formed in the skin is configured to be adjusted by adjusting strength of the current applied to the plurality of needles.

8. The needle tip of claim 5, wherein when the plurality of needles have a plurality of active regions spaced apart from each other, a plurality of energy transfer regions formed between the plurality of active regions are configured to be spread by adjusting the strength of the current applied to the plurality of needles to 20 W to 50 W.

9. The needle tip of claim 8, wherein one of two needles adjacent to each other among the plurality of needles is configured to output a positive (+) polarity, and the other is configured to output a negative (−) polarity.

10. A hand piece, wherein the needle tip according to claim 1, for application of current, is mounted on the hand piece.

11. The needle tip of claim 1, wherein the first insulated region is configured to prevent electrical energy from being transferred to a skin from the tip end of each of the plurality of needles, on which a RF current is concentrated.

12. The needle tip of claim 2, wherein the first insulated region and the second insulated region are physically separated by the active region that is positioned in between the first insulated region and the second insulated region.

* * * * *